United States Patent
Allen et al.

(10) Patent No.: US 7,268,142 B2
(45) Date of Patent: Sep. 11, 2007

(54) TETRAHYDROISOQUINOLINYL DERIVATIVES OF QUINAZOLINE AND ISOQUINOLINE

(75) Inventors: Martin Patrick Allen, Voluntown, CT (US); Thomas Allen Chappie, Old Lyme, CT (US); John Michael Humphrey, Mystic, CT (US); Spiros Liras, Stonington, CT (US); William Michael Whalen, New London, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/062,133

(22) Filed: Feb. 18, 2005

(65) Prior Publication Data

US 2005/0182079 A1 Aug. 18, 2005

Related U.S. Application Data

(60) Provisional application No. 60/545,565, filed on Feb. 18, 2004.

(51) Int. Cl.
*A61K 31/517* (2006.01)
*A61K 31/4725* (2006.01)
*C07D 239/94* (2006.01)
*C07D 217/02* (2006.01)

(52) U.S. Cl. .................. 514/266.21; 514/308; 544/284; 546/140

(58) Field of Classification Search ........... 514/266.21, 514/307, 308; 544/284; 546/139, 140
See application file for complete search history.

(56) References Cited

U.S. PATENT DOCUMENTS 3,674,791 A * 7/1972 Mathison ................... 546/143
5,576,322 A * 11/1996 Takase et al. ........... 514/266.22
5,801,180 A * 9/1998 Takase et al. ........... 514/266.24
2003/0032579 A1 2/2003 Lebel et al. ................. 241/47

FOREIGN PATENT DOCUMENTS

EP 0607439 4/1993
WO 02102315 12/2002

OTHER PUBLICATIONS

Skupinska, K.A. et. al., "Concise Preparation of . . . Hydrogenation of Acetamidoquinolines and Acetamidoisoquinolines." J. Org. Chem., 2002, vol. 67, No. 22, pp. 7890-7093.*
Grunewald, G. L. et. al., "Synthesis and Bochemical Evaluation of 3-Fluoromethyl-1,2,3,4-tetrahydroisoquinoline . . ." J. Med. Chem., 1999, vol. 42, No. 18, pp. 3588-3601.*
Kehler, J. et. al., "The potential therapeutic use of phosphodiesterase 10 inhibitors" Expert Opin. Ther. Patents, 2007, vol. 17, No. 2, pp. 147-158.*
Database Chemcats Chemical Abstracts Service, Columbus, Ohio, US: XP002327094, 2002.
Database Beilstein Beilstein Institut Zur Foerderung Der Chemischen Wissenschaften, Frankfurt Am Main, DE; XP002327095 Database accession No. 12444, 1992.
Aldrich: "Handbook of Fine Chemicals and Laboratory Equipment" 2003, Aldrich, XP002327093.
Beugelmans R et al: "Studies on SRN1 Reactions-9. A New Access to the Isoquinoline Ring System" Tetrahedron, Elsevier Science Publishers, Amsterdam, NL, vol. 40, No. 2, 1984, pp. 311-314, XP002071823 ISSN: 0040-4020.
Katritzky A R et al: "Carbon Dioxide: A Reagent for the Protection of Nuclephilic Centres and The Simulaneous Activation of Electrophilic Attack. Part II. A New Synthetic Method for the 1-Substitution of 1,2,3,4-Thtrahydroisoquinolines" Tetrahedron, Elsevier Science Publishers, Amsterdam, NL, vol. 42, No. 9, 1986, pp. 2571-2574, XP000882952 ISSN: 0040-4020.
Donald J. Brooks et al.: "Isoquinoline-N-Boranes as Prescursors to Substituted Tetrahydroisoquinolines" J. Org. Chem., vol. 49, 1984, pp. 130-133, XP002327091.

* cited by examiner

*Primary Examiner*—James O. Wilson
*Assistant Examiner*—Tamthom N Truong
(74) *Attorney, Agent, or Firm*—Steve Zelson; James A. Jubinsky

(57) ABSTRACT

The invention pertains to substituted quinazoline and isoquinoline compounds that serve as effective phosphodiesterase (PDE) inhibitors. In particular, the invention relates to said compounds which are selective inhibitors of PDE-10. The invention also relates to intermediates for preparation of said compounds; pharmaceutical compositions comprising said compounds; and the use of said compounds in a method for treating certain central nervous system (CNS) or other disorders.

16 Claims, No Drawings

TETRAHYDROISOQUINOLINYL DERIVATIVES OF QUINAZOLINE AND ISOQUINOLINE

This application claims priority under 35 U.S.C. 119(e) of U.S. Provisional 60/545,565, filed Feb. 18, 2004. The entire contents of the prior application U.S. Provisional 60/545,565 is incorporated herein by reference.

FIELD OF THE INVENTION

The invention pertains to substituted quinazoline and isoquinoline compounds that serve as effective phosphodiesterase (PDE) inhibitors. The invention also relates to compounds which are selective inhibitors of PDE-10. The invention further relates to intermediates for preparation of such compounds; pharmaceutical compositions comprising such compounds; and the use of such compounds in methods for treating certain central nervous system (CNS) or other disorders. The invention relates also to methods for treating neurodegenerative and psychiatric disorders, for example psychosis and disorders comprising deficient cognition as a symptom.

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphates (cGMP) into their respective nucleotide monophosphates. The cyclic nucleotides cAMP and cGMP are synthesized by adenylyl and guanylyl cyclases, respectively, and serve as secondary messengers in several cellular pathways.

The cyclic nucleotides, cyclic-adenosine monophosphate (cAMP) and cyclic-guanosine monophosphate (cGMP), function as intracellular second messengers regulating a vast array of intracellular processes particularly in neurons of the central nervous system. In neurons, this includes the activation of cAMP and cGMP dependent kinases and subsequent phosphorylation of proteins involved in acute regulation of synaptic transmission as well as in neuronal differentiation and survival. The complexity of cyclic nucleotide signaling is indicated by the molecular diversity of the enzymes involved in the synthesis and degradation of cAMP and cGMP. There are ten families of adenylyl cyclases, two of guanylyl cyclases, and eleven of phosphodiesterases. Furthermore, different types of neurons are known to express multiple isozymes of each of these classes, and there is good evidence for comparmentalization and specificity of function for different isozymes within a given neuron.

A principal mechanism for regulating cyclic nucleotide signaling is by phosphodiesterase-catalyzed cyclic nucleotide catabolism. There are eleven known families of PDEs encoded by 21 different genes. Each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE families or isozymes may offer particular therapeutic effects, fewer side effects, or both.

PDE10 is identified as a unique family based on primary amino acid sequence and distinct enzymatic activity. Homology screening of EST databases revealed mouse PDE10A as the first member of the PDE10 family of PDEs (Fujishige et al., J. Biol. Chem. 274:18438-18445, 1999; Loughney, K. et al., Gene 234:109-117, 1999). The murine homologue has also been cloned (Soderling, S. et al., Proc. Natl. Acad. Sci. USA 96:7071-7076, 1999) and N-terminal splice variants of both the rat and human genes have been identified (Kotera, J. et al., Biochem. Biophys. Res. Comm. 261:551-557, 1999; Fujishige, K. et al., Eur. J. Biochem. 266:1118-1127, 1999). There is a high degree of homology across species. The mouse PDE10A1 is a 779 amino acid protein that hydrolyzes both cAMP and cGMP to AMP and GMP, respectively. The affinity of PDE10 for cAMP ($Km=0.05$ μM) is higher than for cGMP ($Km=3$ μM). However, the approximately 5-fold greater Vmax for cGMP over cAMP has lead to the suggestion that PDE10 is a unique cAMP-inhibited cGMPase (Fujishige et al., J. Biol. Chem. 274:18438-18445, 1999).

The PDE 10 family of polypeptides shows a lower degree of sequence homology as compared to previously identified PDE families and has been shown to be insensitive to certain inhibitors that are known to be specific for other PDE families. U.S. Pat. No. 6,350,603.

PDE10 also is uniquely localized in mammals relative to other PDE families. mRNA for PDE10 is highly expressed only in testis and brain (Fujishige, K. et al., Eur J. Biochem. 266:1118-1127, 1999; Soderling, S. et al., Proc. Natl. Acad. Sci. 96:7071-7076, 1999; Loughney, K. et al., Gene 234: 109-117, 1999). These initial studies indicated that within the brain PDE10 expression is highest in the striatum (caudate and putamen), n. accumbens, and olfactory tubercle. More recently, a detailed analysis has been made of the expression pattern in rodent brain of PDE10 mRNA (Seeger, T. F. et al., Abst. Soc. Neurosci. 26:345. 10, 2000) and PDE10 protein (Menniti, F. S., Stick, C. A., Seeger, T. F., and Ryan, A. M., Immunohistochemical localization of PDE10 in the rat brain. William Harvey Research Conference 'Phosphodiesterase in Health and Disease', Porto, Portugal, Dec. 5-7, 2001).

A variety of therapeutic uses for PDE inhibitors has been reported including obtrusive lung disease, allergies, hypertension, angina, congestive heart failure, depression and erectile dysfunction (WO 01/41807 A2).

The use of selected benzimidazole and related heterocyclic compounds in the treatment of ischemic heart conditions has been disclosed based upon inhibition of PDE associated cGMP activity. U.S. Pat. No. 5,693,652.

U.S. Patent Application Publication No. 2003/0032579 discloses a method for treating certain neurologic and psychiatric disorders with the selective PDE10 inhibitor papaverine. In particular, the method relates to psychotic disorders such as schizophrenia, delusional disorders and drug induced psychosis; to anxiety disorders such as panic and obsessive-compulsive disorder; and to movement disorders including Parkinson's disease and Huntington's disease.

SUMMARY OF THE INVENTION

In one aspect, the invention relates to compounds having the following formula, denoted herein as formula I:

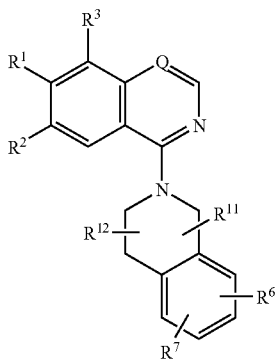

and to pharmaceutically acceptable salts, solvates and prodrugs thereof, wherein Q is N or CH;

wherein $R^1$, $R^2$ and $R^3$ are each independently hydrogen, halogen, $(C_1-C_9)$alkyl, $(C_2-C_9)$ alkenyl, $(C_2-C_9)$ alkynyl, $(C_3-C_8)$cycoloalkyl, —O-$(C_1-C_9)$ alkyl, —O-$(C_2-C_9)$—O—$(C_2-C_9)$ alkenyl, $(C_1-C_6)$alkyl O—$(C_1-C_6)$alkyl, —C≡N, —NO$_2$, —COOR$^4$, —CONR$^4$R$^5$, —NR$^4$R$^5$, —COR$^5$, or —COOH wherein said alkyl, alkenyl and alkynyl are optionally substituted with 1 to 3 halogens; wherein $R^4$ and $R^5$ are independently H, $C_1-C_6$ alkyl, or $(C_2-C_6)$alkenyl) wherein said alkyl and alkenyl are optionally substituted with from 1 to 3 halogen atoms; and, when $R^1$, $R^2$ and $R^3$ are independently —O-alkyl, —O-alkenyl, or alkyl, alkenyl or alkynyl, $R^1$ and $R^2$, or $R^1$ and $R^3$, may optionally be connected to form a 5 to 6 membered ring;

$R^6$ and $R^7$ are independently hydrogen;

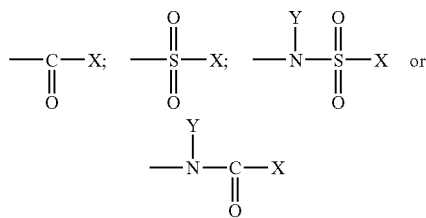

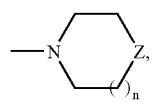

wherein X is a $C_1-C_6$ alkyl group unsubstituted or substituted with one or more halogens, —O—$C_1-C_6$ alkyl unsubstituted or substituted with one or more halogens, a $(C_6-C_{14})$ aryl group unsubstituted or substituted with one or two substituents, a —NR$^8$R$^9$ group or wherein said $(C_6-C_{14})$ aryl group substituents are independently selected from $C_1-C_6$ alkyl, —O—$C_1-C_6$ alkyl, halogen, —C≡N, —NO$_2$, —COOR$^4$, —CONR$^4$R$^5$, —NR$^4$R$^5$, —COR$^4$, and —COOH, and $(C_1-C_6)$alkyl substituted with 1 to 3 halogens;

Y is hydrogen or $(C_1-C_6)$alkyl;

n is 0 or 1;

$R^8$ and $R^9$ are each independently $(C_1-C_6)$alkyl or hydrogen;

Z is oxygen or NR$^{10}$, wherein R$^{10}$ is hydrogen or $(C_1-C_6)$alkyl;

wherein $R^{11}$ and $R^{12}$ are independently H, halogen, C≡N, —COOH, —COOR$^4$, —CONR$^4$R$^5$, COR$^4$, —NR$^4$R$^5$, —OH, $(C_6-C_{14})$aryl, 5 to 12 membered heteroaryl, $(C_1-C_6)$ alkyl, $(C_2-C_6)$ alkenyl, $(C_2-C_6)$ alkynyl or $(C_3-C_8)$ cycloalkyl wherein said alkyl, alkenyl, and alkynyl are optionally independently substituted with from 1 to 3 halogens.

A particular embodiment of the invention relates to compounds of the formula I wherein Q is N and $R^1$ and $R^2$ are each —OCH$_3$.

Another embodiment of this invention relates to compounds of the formula I wherein Q is N, $R^1$ and $R^2$ are each —OCH$_3$ and one or both of $R^6$ and $R^7$ are

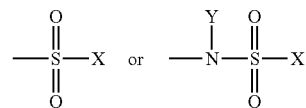

wherein X and Y are as defined above.

A preferred embodiment of this invention relates to compounds of formula I wherein Q is N, $R^1$ and $R^2$ are each —OCH$_3$, and one or both of $R^6$ and $R^7$ are

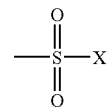

and X is 4-methyl piperazine.

Another preferred embodiment of this invention relates to compounds of formula I wherein Q is N, $R^1$ and $R^2$ are each —OCH$_3$ and one or both of $R^6$ and $R^7$ are

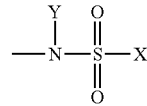

wherein X is mono-or disubstituted aryl and Y is hydrogen. Preferably aryl is phenyl or naphthyl, optionally substituted with $C_1-C_6$ alkyl, $C_1-C_6$ alkoxy, —C≡N, —NO$_2$, —COOR$^4$, —CONR$^4$R$^5$, —NR$^4$R$^5$, —COR$^4$, and —COOH, wherein $R^4$ and $R^5$ are as defined above.

Another embodiment of this invention relates to compounds of formula 1 wherein Q is N, $R^1$ and $R^2$ are each —OCH$_3$ and one or both of $R^6$ and $R^7$ is

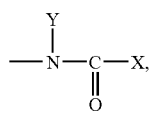

wherein X and Y are as defined above.

Another embodiment of the present invention relates to compounds of formula I wherein Q is CH, $R^1$ and $R^2$ are each —$OCH_3$ and $R^6$, $R^7$, $R^{11}$ and $R^{12}$ are hydrogen.

In another embodiment, $R^{11}$ and $R^{12}$ are independently selected from hydrogen, ($C_1$-$C_6$)alkyl, ($C_2$-$C_6$)alkenyl, ($C_2$-$C_6$)alkynyl, and ($C_3$-$C_8$) cycloalkyl. In such embodiment, Q is preferably N.

Examples of specific compounds of the formula I are the following:

N-[2-(6,7-dimethoxy-quinazolin-4-yl)-1,2,3,4-tetrahydro-isoquinolin-7-yl]4-isopropyl-benzenesulfonamide;
N-[2-(6,7-dimethoxy-quinazolin-4-yl)-1,2,3,4-tetrahydro-isoquinolin-7-yl]-2,5-dimethyl-benzenesulfoamide;
N-[2-(6,7-dimethoxy-quinazolin-4-yl)-1,2,3,4-tetrahydro-isoquinolin-7-yl]-2,2-dimethyl-propionamide;
N-[2-(6,7-dimethoxy-quinazoline-4-yl)-1,2,3,4-tetrahydro-isoquinolin-7-yl]-acetamide;
4-chloro-N-[2-(6,7-dimethoxy-quinazolin-4-yl)-1,2,3,4-tetrahydro-isoquinolin-7-yl]-benzenesulfonamide;
N-[2-(6,7-dimethoxy-quinazoline-4-yl)-1,2,3,4-tetrahydro-isoquinolin-7-yl]-acetamide;
N-[2-(6,7-dimethoxy-quinazolin-4-yl)-1,2,3,4-tetrahydro-isoquinolin-7-yl]-4-ethyl-benzamide;
4-chloro-N-[2-(6,7-dimethoxy-quinazolin-4-yl)-1,2,3,4-tetrahydro-isoquinolin-7-yl]-benzamide;
3-chloro-N-[2-(6,7-dimethoxy-quinazolin-4-yl)-1,2,3,4-tetrahydro-isoquinolin-7-yl]-benzamide;
4-tert-butyl-N-[2-(6,7-dimethoxy-quinazolin-4-yl)-1,2,3,4-tetrahydro-isoquinolin-7-yl]-benzenesulfonamide;
N-[2-(6,7-dimethoxyquinazolin-4-yl)-1,2,3,4-tetrahydroisoquinolin-7-yl]-4-ethoxy benzamide;
N-[2-(6,7-dimethoxy-quinazolin-4-yl)-1,2,3,4-tetrahydro-isoquinolin-7-yl]-4-trifluoromethyl-benzenesulfonamide;
N-[2-(6,7-dimethoxy-quinazolin-4-yl)-1,2,3,4-tetrahydro-isoquinolin-7-yl]-3,4-dimethoxy-benzenesulfonamide;
6,7-dimethoxy-4-[8-(morpholine-4-sulfonyl)-3,4-dihydro-1H-isoquinolin-2-yl]-quinazoline;
6,7-dimethoxy-4-[8-(4-methyl-piperazine-1-sulfonyl)-3,4-dihydro-1H-isoquinolin-2-yl]-quinazoline;
4-(7,8-dimethoxy-3,4-dihydro-1H-isoquinolin-2-yl)-6-ethoxy-7-methoxy-quinazoline;
4-(6,7-dimethoxy-3,4-dihydro-1H-isoquinolin-2-yl)-6-ethoxy-7-methoxy-quinazoline;
4-(6,7-dimethoxy-3-methyl-3,4-dihydro-1H-isoquinolin-2-yl)-6-ethoxy-7-methoxy-quinazoline;
4-(3,4-dihydro-1H-isoquinolin-2-yl)-6-ethoxy-7-methoxy-quinazoline;
4-(3,4-dihydro-1H-isoquinolin-2-yl)-7-methoxy-quinazoline;
2-(6,7-dimethoxy-quinazolin-4-yl)-1,2,3,4-tetrahydro-isoquinolin-7-ylamine;
6,7-dimethoxy-3',4'-dihydro-1H-[1,2]biisoquinolinyl; and
6,7-dimethoxy-4-(3-propyl-3,4-dihydro-1H-isoquinolin-2-yl)-quinazoline.

The following are preferred compounds which may be made by methods disclosed herein.

6,7,8-Trimethoxy-4-[8-(4-methyl-piperazine-1-sulfonyl)-3,4-dihydro-1H-isoquinolin-2-yl]-quinazoline
4-Methoxy-6-[8-(4-methyl-piperazine-1-sulfonyl)-3,4-dihydro-1H-isoquinolin-2-yl]-1,3-dioxa-7,9-diaza-cyclopenta[a]naphthalene
6,7,8-Trimethoxy-4-(8-methoxy-3,4-dihydro-1H-isoquinolin-2-yl)-quinazoline
4-Methoxy-6-(8-methoxy-3,4-dihydro-1H-isoquinolin-2-yl)-1,3-dioxa-7,9-diaza-cyclopenta[a]naphthalene
2-(4-Methoxy-1,3-dioxa-7,9-diaza-cyclopenta[a]naphthalen-6-yl)-1,2,3,4-tetrahydro-isoquinoline-7-carboxylic acid amide
2-(6,7,8-Trimethoxy-quinazolin-4-yl)-1,2,3,4-tetrahydro-isoquinoline-7-carboxylic acid amide
6,7,8-Trimethoxy-4-[6-(4-methoxy-phenyl)-3,4-dihydro-1H-isoquinolin-2-yl]-quinazoline
4-Methoxy-6-[6-(4-methoxy-phenyl)-3,4-dihydro-1H-isoquinolin-2-yl]-1,3-dioxa-7,9-diaza-cyclopenta[a]naphthalene The above listed compounds and their pharmaceutically salts, solvates, and prodrugs thereof are preferred embodiments of the subject invention.

This invention also pertains to a pharmaceutical composition for treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease, comprising an amount of a compound of formula I effective in inhibiting PDE 10.

In another embodiment, this invention relates to a pharmaceutical composition for treating psychotic disorders and condition such as schizophrenia, delusional disorders and drug induced psychosis; anxiety disorders such as panic and obsessive-compulsive disorder; and movement disorders including Parkinson's disease and Huntington's disease, comprising an amount of a compound of formula I effective in treating said disorder or condition.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

Examples of movement disorders that can be treated according to the present invention include but are not limited to selected from Huntington's disease and dyskinesia associated with dopamine agonist therapy, Parkinson's disease, restless leg syndrome, and essential tremor.

Other disorders that can be treated according to the present invention are obsessive/compulsive disorders, Tourette's syndrome and other tic disorders.

In another embodiment, this invention relates to a method for treating an anxiety disorder or condition in a mammal which method comprises administering to said mammal an amount of a compound of formula I effective in inhibiting PDE 10.

This invention also provides a method for treating an anxiety disorder or condition in a mammal which method comprises administering to said mammal an amount of a compound of formula I effective in treating said disorder or condition.

Examples of anxiety disorders that can be treated according to the present invention include, but are not limited to, panic disorder; agoraphobia; a specific phobia; social phobia; obsessive-compulsive disorder; post-traumatic stress disorder; acute stress disorder; and generalized anxiety disorder.

This invention further provides a method of treating a drug addiction, for example an alcohol, amphetamine, cocaine, or opiate addiction, in a mammal, including a human, which method comprises administering to said mammal an amount of a compound of formula I effective in treating drug addiction.

This invention also provides a method of treating a drug addiction, for example an alcohol, amphetamine, cocaine, or opiate addiction, in a mammal, including a human, which method comprises administering to said mammal an amount of a compound of formula I effective in inhibiting PDE10.

A "drug addiction", as used herein, means an abnormal desire for a drug and is generally characterized by motivational disturbances such a compulsion to take the desired drug and episodes of intense drug craving.

This invention further provides a method of treating a disorder comprising as a symptom a deficiency in attention and/or cognition in a mammal, including a human, which method comprises administering to said mammal an amount of a compound of formula I effective in treating said disorder.

This invention also provides a method of treating a disorder or condition comprising as a symptom a deficiency in attention and/or cognition in a mammal, including a human, which method comprises administering to said mammal an amount of a compound of formula I effective in inhibiting PDE10.

This invention also provides a method of treating a disorder or condition comprising as a symptom a deficiency in attention and/or cognition in a mammal, including a human, which method comprises administering to said mammal an amount of a compound of formula I effective in treating said disorder or condition.

The phrase "deficiency in attention and/or cognition" as used herein in "disorder comprising as a symptom a deficiency in attention and/or cognition" refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as occurs in age-related cognitive decline.

Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a mood disorder or mood episode in a mammal, including a human, comprising administering to said mammal an amount of a compound of formula I effective in treating said disorder or episode.

This invention also provides a method of treating a mood disorder or mood episode in a mammal, including a human, comprising administering to said mammal an amount of a compound of formula I effective in inhibiting PDE10.

Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

This invention further provides a method of treating a neurodegenerative disorder or condition in a mammal, including a human, which method comprises administering to said mammal an amount of a compound of formula I effective in treating said disorder or condition.

This invention further provides a method of treating a neurodegenerative disorder or condition in a mammal, including a human, which method comprises administering to said mammal an amount of a compound of formula I effective in inhibiting PDE10.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temperal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition comprises neurodegeneration of striatal medium spiny neurons in a mammal, including a human.

In a further embodiment of the present invention, the neurodegenerative disorder or condition is Huntington's disease.

The term "aryl", as used herein, unless otherwise indicated, includes an organic radical derived from a univalent aromatic hydrocarbon and includes but is not limited to, phenyl, naphthyl and indenyl.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "cycloalkyl", as used herein, unless otherwise indicated, includes alkyl groups comprising non-aromatic saturated cyclic alkyl moieties wherein alkyl is as defined above. Examples of cycloalkyl include, but are not limited to, cyclopropyl, cyclopropylethyl, cyclopropylmethyl, cyclobutyl, cyclopentyl, cyclohexyl, and cycloheptyl.

"Heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

"Neurotoxin poisoning" refers to poisoning caused by a neurotoxin. A neurotoxin is any chemical or substance that can cause neural death and thus neurological damage. An example of a neurotoxin is alcohol, which, when abused by a pregnant female, can result in alcohol poisoning and neurological damage known as Fetal Alcohol Syndrome in a newborn. Other examples of neurotoxins include, but are not limited to, kainic acid, domoic acid, and acromelic acid; certain pesticides, such as DDT; certain insecticides, such as organophosphates; volatile organic solvents such as hexacarbons (e.g. toluene); heavy metals (e.g. lead, mercury, arsenic, and phosphorous); aluminum; certain chemicals used as weapons, such as Agent Orange and Nerve Gas; and neurotoxic antineoplastic agents.

As used herein, the term "selective PDE10 inhibitor" refers to a substance, for example an organic molecule, that effectively inhibits an enzyme from the PDE10 family to a greater extent than enzymes from the PDE 1-9 families or PDE11 family. In one embodiment, a selective PDE10 inhibitor is a substance, for example an organic molecule, having a $K_i$ for inhibition of PDE10 that is less than or about one-tenth the $K_i$ that the substance has for inhibition of any other PDE enzyme. In other words, the substance inhibits PDE10 activity to the same degree at a concentration of about one-tenth or less than the concentration required for any other PDE enzyme.

In general, a substance is considered to effectively inhibit PDE10 activity if it has a $K_i$ of less than or about 10 μM, preferably less than or about 0.1 μM.

A "selective PDE10 inhibitor" can be identified, for example, by comparing the ability of a substance to inhibit PDE10 activity to its ability to inhibit PDE enzymes from the other PDE families. For example, a substance may be assayed for its ability to inhibit PDE10 activity, as well as PDE1, PDE2, PDE3A, PDE4A, PDE4B, PDE4C, PDE4D, PDE5, PDE6, PDE7, PDE8, PDE9, and PDE11.

The term "treating", as in "a method of treating a disorder", refers to reversing, alleviating, or inhibiting the progress of the disorder to which such term applies, or one or more symptoms of the disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder.

For example, "treating schizophrenia, or schizophreniform or schizoaffective disorder" as used herein also encompasses treating one or more symptoms (positive, negative, and other associated features) of said disorders, for example treating, delusions and/or hallucination associated therewith. Other examples of symptoms of schizophrenia and schizophreniform and schizoaffecctive disorders include disorganized speech, affective flattening, alogia, anhedonia, inappropriate affect, dysphoric mood (in the form of, for example, depression, anxiety or anger), and some indications of cognitive dysfunction.

The term "mammal", as used herein, refers to any member of the class "Mammalia", including, but not limited to, humans, dogs, and cats.

This invention also pertains to an intermediate compound of formula III and its derivatives which are used in the preparation of compounds of formula I

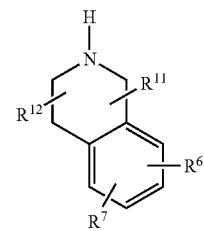

III wherein one or both of $R^6$ and $R^7$ are hydrogen,

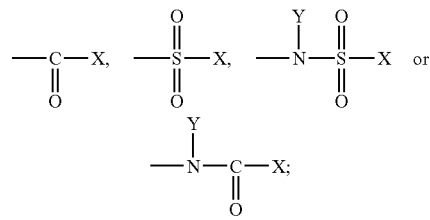

wherein X is a $C_1$-$C_6$ alkyl group unsubstituted or substituted with one or more halogens, a $C_1$-$C_6$ alkoxy group unsubstituted or substituted with one or more halogens, a $(C_6$-$C_{14})$ aryl group unsubstituted or substituted with one or two substituents, a —$NR^8R^9$ group or

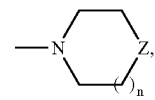

wherein said $(C_6$-$C_{14})$ aryl group substituents are independently selected from $C_1$-$C_6$ alkyl, $C_1$-$C_6$ alkoxy, halogen, —C≡N, —$NO_2$, —$COOR^4$, —$CONR^4R^5$, —$NR^4R^5$, —$COR^4$, and —COOH, and $(C_1$-$C_6)$alkyl substituted with 1 to 3 halogens;

Y is hydrogen or $(C_1-C_6)$alkyl;

n is 0 or 1;

$R^8$ and $R^9$ are each independently $(C_1-C_6)$alkyl or hydrogen; and

Z is oxygen or $NR^{10}$, wherein $R^{10}$ is hydrogen or $(C_1-C_6)$alkyl.

wherein $R^{11}$ and $R^{12}$ are independently H, halogen, C≡N, —COOH, —COOR$^3$, —CONR$^3$R$^4$, COR$^3$, —NR$^3$R$^4$, —OH, $(C_6-C_{14})$aryl, 5 to 12 membered heteroaryl, $(C_1-C_6)$ alkyl, $(C_2-C_6)$ alkenyl, $(C_2-C_6)$ alkynyl or $(C_3-C_8)$ cycloalkyl wherein said alkyl, alkenyl, and alkynyl are optionally independently substituted with from 1 to 3 halogens;

In another embodiment the present invention relates to a process for preparing a compound of formula I

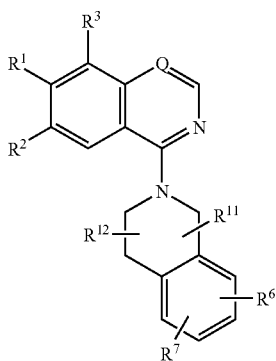

and to pharmaceutically acceptable salts, solvates and prodrugs thereof, wherein Q is N or C;

wherein $R^1$ and $R^2$ are each independently hydrogen, halogen, $(C_1-C_9)$alkyl, $(C_2-C_9)$ alkenyl, $(C_2-C_9)$ alkynyl, $(C_3-C_8)$cycloalkyl, —O—$(C_1-C_9)$ alkyl, —O—$(C_2-C_9)$ alkenyl, $(C_1-C_6)$alkoxy $(C_1-C_6)$alkyl, —C≡N, —NO$_2$, —COOR$^4$, —CONR$^4$R$^5$, —NR$^4$R$^5$, —COR$^5$, —COOH wherein said alkyl, alkenyl and alkynyl are optionally substituted with 1 to 3 halogens, wherein $R^4$ and $R^5$ are independently H or $C_1-C_6$ alkyl optionally substituted with from 1 to 3 halogen atoms; and, when $R^1$ and $R^2$ are independently —O-alkyl or alkyl, $R^1$ and $R^2$ may be connected to form a 5 to 6 membered ring;

one or both of $R^6$ and $R^7$ are hydrogen;

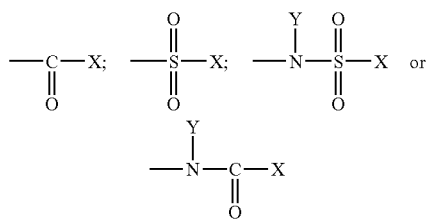

wherein X is a $C_1-C_6$ alkyl group unsubstituted or substituted with one or more halogens, a $C_1-C_6$ alkoxy group unsubstituted or substituted with one or more halogens, a $(C_6-C_{14})$ aryl group unsubstituted or substituted with one or two substituents, a —NR$^8$R$^9$ group or

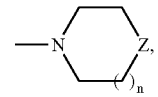

wherein said $(C_6-C_{14})$ aryl group substituents are independently selected from $C_1-C_6$ alkyl, $C_1-C_6$ alkoxy, halogen, —C≡N, —NO$_2$, —COOR$^4$, —CONR$^4$R$^5$, —NR$^4$R$^5$, —COR$^4$, and —COOH, and $(C_1-C_6)$alkyl substituted with 1 to 3 halogens;

Y is hydrogen or $(C_1-C_6)$alkyl;

n is 0 or 1;

$R^8$ and $R^9$ are each independently $(C_1-C_6)$alkyl or hydrogen;

Z is oxygen or $NR^{10}$, wherein $R^{10}$ is hydrogen or $(C_1-C_6)$alkyl;

wherein $R^{11}$ and $R^{12}$ are independently H, halogen, C≡N, —COOH, —COOR$^4$, —CONR$^4$R$^5$, COR$^4$, —NR$^4$R$^5$, —OH, $(C_6-C_{14})$aryl, 5 to 12 membered heteroaryl, $(C_1-C_6)$ alkyl, $(C_2-C_6)$ alkenyl, $(C_2-C_6)$ alkynyl or $(C_3-C_8)$ cycloalkyl wherein said alkyl, alkenyl, and alkynyl are optionally independently substituted with from 1 to 3 halogens;

comprising reacting a compound of formula II$_a$

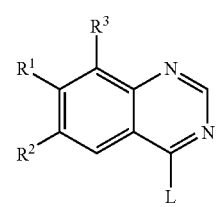

wherein $R^1$ and $R^2$ are each independently hydrogen, halogen, $(C_1-C_9)$alkyl, $(C_2-C_9)$ alkenyl, $(C_2-C_9)$ alkynyl, $(C_3-C_8)$cycoloalkyl, —O—$(C_1-C_9)$ alkyl, —O—$(C_2-C_9)$ alkenyl, $(C_1-C_6)$alkoxy $(C_1-C_6)$alkyl, —C≡N, —NO$_2$, —COOR$^4$, —CONR$^4$R$^5$, —NR$^4$R$^5$, —COR$^5$, —COOH wherein said alkyl, alkenyl and alkynyl are optionally substituted with 1 to 3 halogens, wherein $R^4$ and $R^5$ are independently H or $C_1-C_6$ alkyl optionally substituted with from 1 to 3 halogen atoms; and, when $R^1$, $R^2$ and $R^3$ are independently —O-alkyl or alkyl, $R^1$ and $R^2$ or $R^1$ and $R^3$ may be connected to form a 5 to 6 membered ring;

and L is a suitable leaving group; with a compound of formula III

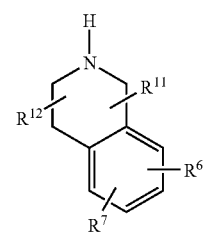

wherein $R^5$, $R^6$, $R^{10}$ and $R^{11}$ are defined above, preferably in the presence of a base.

Examples of leaving groups include, but are not limited to chlorine, bromine, iodine, p-toluenesulfonate, alkyl sulfate and alkanesulfonate, particularly trifluoromethanesulfonate.

In a preferred embodiment, the leaving group L is chlorine.

DETAILED DESCRIPTION OF THE INVENTION

The tetrahydroisoquinolinyl substituted quinazoline compounds of formula I of the invention may be prepared as described in the following reaction schemes and discussion. Unless otherwise indicated, in the reaction schemes and discussion that follow, $R^1$ through $R^8$, X, Y and Z are as defined above.

Scheme 1 below illustrate a general method for preparing compounds of formula I by coupling the 4-chloro substituted quinazoline II with a selected derivative of tetrahydroisoquinoline of formula III.

SCHEME 1

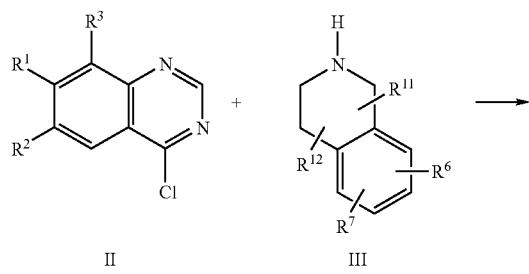

Scheme 2 depicts a coupling reaction between 4-chloro-6,7-dimethoxyquinazoline [PC Int. Appl. 2003008388, 30 Jan. 2003] and an $R^3$ derivative of tetrahydroisoquinoline to generate the dimethoxy substituted compound of formula I. This reaction is typically carried out in an inert solvent such as, for example, toluene, optionally in the presence of a carbonate base, at a temperature range of from about 0° C. to about 200° C. Other suitable solvents include benzene, chloroform, dioxane, ethyl acetate, 2-propanol and xylene. Alternatively, solvent mixtures such as toluene/isopropanol can be used. Preferably the reactants are heated under reflux in a solvent mixture of toluene and isopropanol for a period of from about 2 hours to about 24 hours.

Schemes 3, 4, 5A, 5B, 6 and 7 below illustrate specific synthetic routes to representative intermediates of formula III.

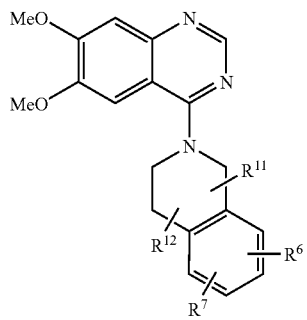

SCHEME 3

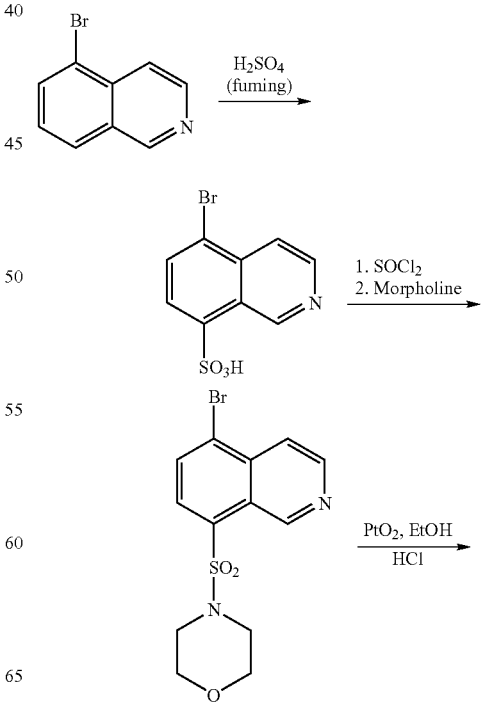

SCHEME 2

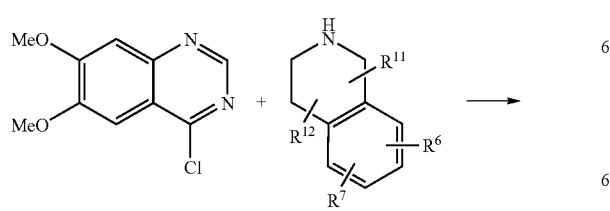

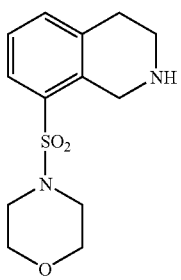

Scheme 3 illustrates a method for preparing 8-(aminosulfonyl)-substituted tetrahydroisoquinolines. The scheme illustrates the use of morpholine as the amino-component, but it is recognized that morpholine can be substituted with any one of a variety of cyclic and acyclic amines. 5-bromoisoquinoline is prepared according to literature procedures (Brown, W. D. and A.-H. Gouliaev, Synthesis, 2002. 1: p. 83-86; Rey, M., T. Vergnani, and A. S. Dreiding, Helv. Chim. Acta. 1985. 68: p. 1828-1834.) Sulfonation is accomplished via treatment with fuming sulfuric acid. Treatment with thionyl chloride neat or in an inert solvent provides the sulfonyl chloride. The sulphonyl chloride can be isolated prior to the next step. Preferably, the sulfonyl chloride is treated in situ with the desired amine component to generate the 5-bromo-8-aminosulfonylquinazoline. Catalytic hydrogenation under one of many possible sets of conditions known to those skilled in the art is used to cleave the bromine atom and reduce the isoquinoline to the tetrahydroisoquinoline.

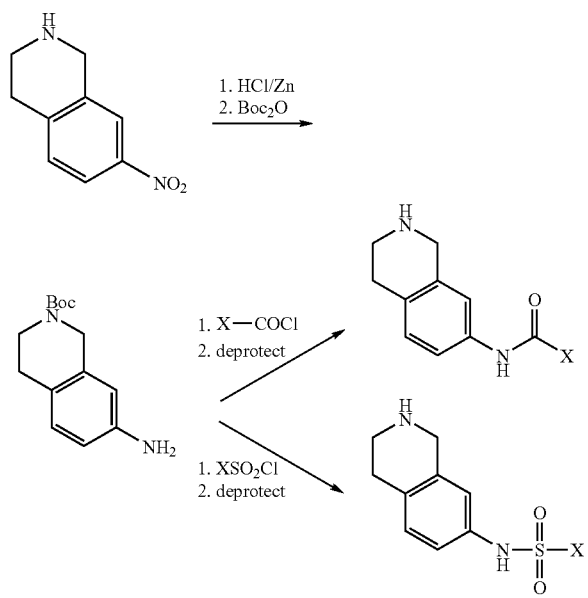

SCHEME 4

The tetrahydroisoquinolin-7-yl-alkanamides and the tetrahydroisoquinolin-7-yl-alkane sulfonamides depicted in Scheme 4 are prepared from 7-nitro-1,2,3,4-tetrahydroisoquinoline. (McCoubrey, A. M. and D. W. Mathieson, J. Chem. Soc., 1951: p. 2851-2853.) Reduction of the nitro group to the aniline can be accomplished by catalytic hydrogenation or via zinc reduction in the presence of acid. Preferably, reduction with zinc in aqueous HCl is employed. The resultant tetrahydroisoquinolin-7-yl-amine is protected via acylation which occurs preferentially at the tetrahydroisoquinoline nitrogen atom. Tert-butyloxycarbonyl protection is generally employed, although it is understood that other carbamate protecting groups, such as Cbz or Fmoc, can also be used. Alternative protection schemes include but are not limited to acetylation and trifluoroacetylation. The acylation reaction is typically performed in an inert solvent in the presence of base. Alternatively, base could be omitted since the substrate possesses an aniline group that could serve as an internal base. After protection, the substrate can be treated with acyl chlorides and sulfonyl chlorides to generate the corresponding alkanamides and sufonamides. Finally, cleavage of the protecting group is conducted according to standard conditions known to those skilled in the art to give the tetrahydroisoquinoline products.

SCHEME 4B:

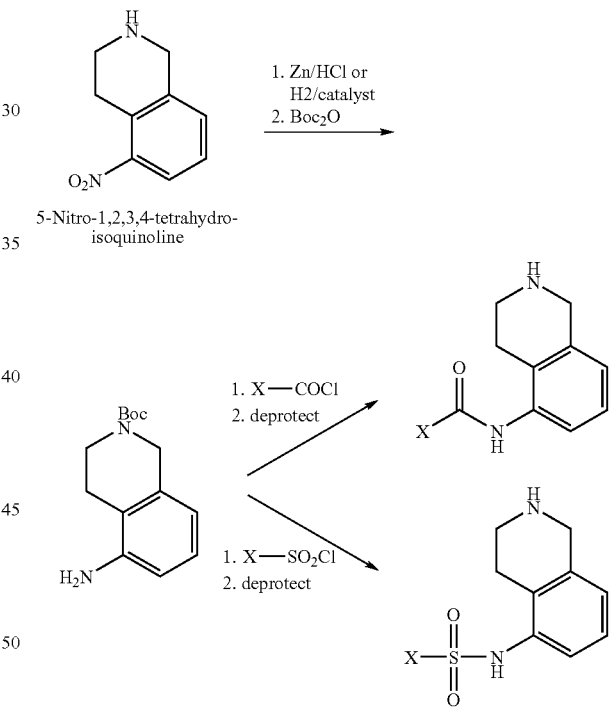

In a similar fashion, 5-nitro-1,2,3,4-tetrahydro-isoquinoline[2] is reduced the the corresponding aniline and protected with an appropriate group as described in Scheme 4. The order of these transformations could be reversed such that the protection step precedes the reduction step. Both steps are well-known and easily conducted according to standard procedures. Conversion into the corresponding tetrahydroisoquinolin-5-yl acetamides and sulfonamides is accomplished in a straightforward manner via treatment with the appropriate acyl or sulfonyl chloride followed by subsequent deprotection in the same manner as described for Scheme 4.

SCHEME 4C

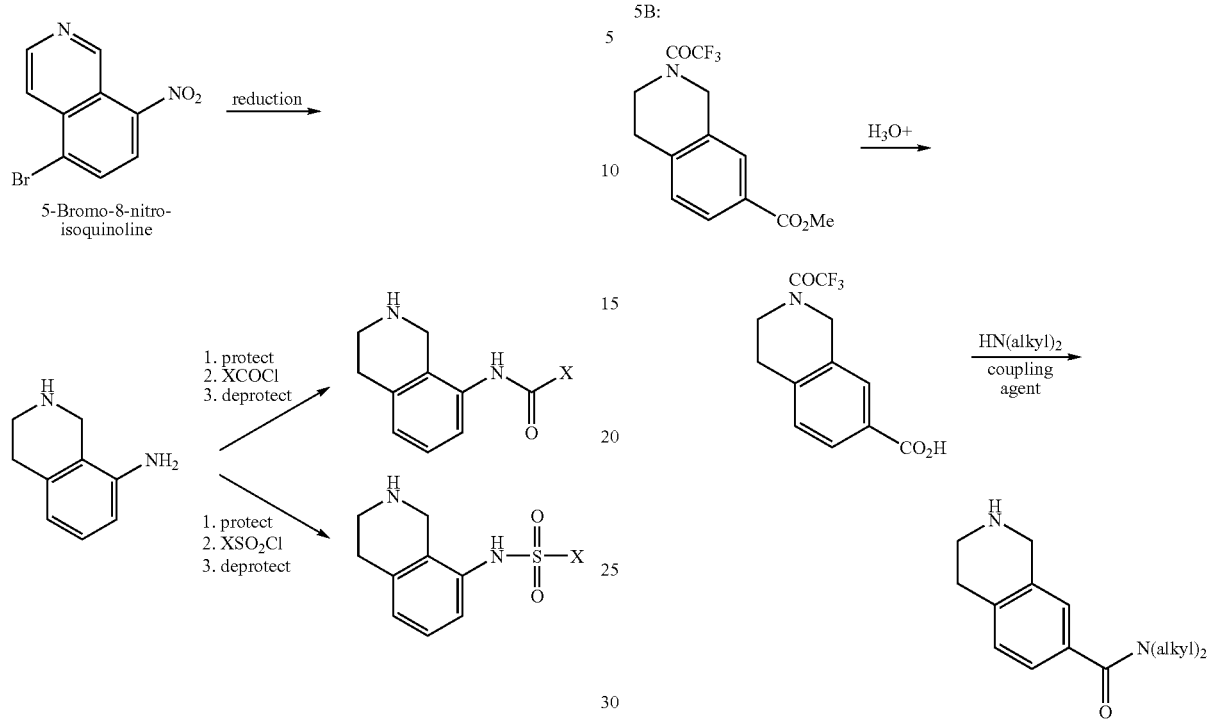

Scheme 4C depicts a method for the synthesis of tetrahydroisoquinolin-8-yl acetamides and sulfonamides. According to this method, 5-bromo-8-nitroisoquinoline[3] is reduced to 8-amino-1,2,3,4-tetrahydroisoquinoline via sequential catalytic hydrogenation of the isoquinoline ring and zinc-HCl reduction of the nitro group according to standard conditions as described herein. Conversion into the corresponding amides and sulfonamides requires prior protection with a suitable carbamate group, such as the Boc group. Subsequent treatment with the appropriate acyl- and sulfonyl chlorides and deprotection according to the usual conditions yields the products.

SCHEME 5A/5B

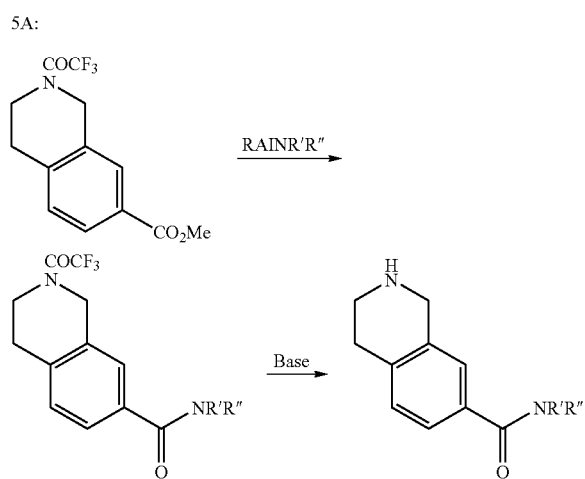

The 1,2,3,4-tetrahydro-isoquinoline-7-carboxylic acid alkanamides can be prepared from 2-(2,2,2-trifluoro-acetyl)-1,2,3,4-tetrahydro-isoquinoline-7-carboxylic acid methyl ester. (Stoker, G. E., Tetrahedron Lett., 1996. 37(31): p. 5453-5456.)

In one method, known as the Weinreb amidation and shown in Scheme 5A, the ester is treated with dialkylaluminum amides according to the procedure of Basha, A., M. Lipton, and S. M. Weinreb, Tetrahedron, 1977. 48: p. 4171-4174.

Other methods, shown in Scheme 5B, require hydrolysis of the ester to produce the carboxylic acid. The acid can then be coupled with amine components utilizing methods well known to those skilled in the art. For example, this can be done via conversion of the carboxylic acid into the acid chloride under commonly known conditions. The acid chloride is then treated with the amine component in the presence of base in an inert solvent such as methylene chloride to provide the amide product. This coupling can also be mediated by specialized coupling reagents known to those skilled in the art, such as DCC, HATU, BOP-Cl, PyBrop and many others. (Humphrey, J. M. and A. R. Chamberlin, Chem. Rev., 1997. 97(6): p. 2243-2266 and Bodanszky, M., Principles of Peptide Synthesis. 2nd ed. 1993, Berlin Heidelberg: Springer-Verlag.) Suitable solvents for couplings via the acid chloride or coupling agent-mediated reactions include methylene chloride, chloroform, TCE, benzene, toluene, THF, DMF, dioxane and glyme among others. Subsequent to amide bond formation, the trifluoroacetyl group is removed via treatment with a carbonate or hydroxide base according to the usual conditions to generate the substituted tetrahydroisoquinoline.

SCHEME 6

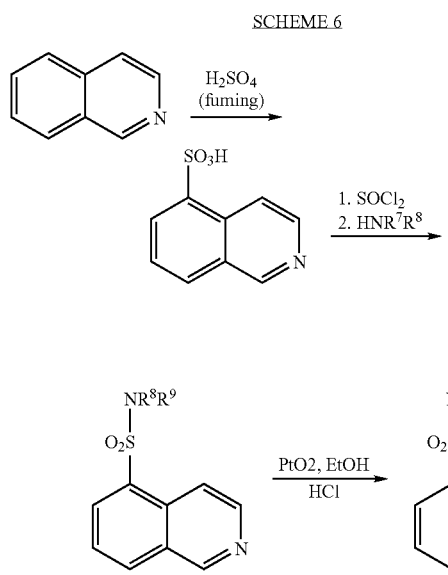

Scheme 6 depicts a method for the synthesis of 5-aminosulfonyl tetrahydroisoquinolines. 5-isoquinoline sulfonic acid is prepared via treatment of isoquinoline with fuming sulfuric acid as described in the literature. (Koelsch, C. F. and N. F. Albertson, J. Am. Chem. Soc., 1953. 75: p. 2095-2097).

The corresponding sulfonyl chloride is prepared via treatment with thionyl chloride. (Morikawa, A., T. Sone, and T. Asano, J. Med. Chem., 1989. 32: p. 42-46.)

Other reagents, such as phosphorous pentoxide, may also be used for this transformation. Coupling with amine components and subsequent reduction to generate a tetrahydroisoquinoline compound of formula I accomplished as in Scheme 1.

Scheme 7 depicts a method for the conversion of an aryl sulfonyl chloride to an alkyl sulfone. According to this literature method, the sulfonyl chloride is treated with iron powder followed by an alkyl halide. To the mixture is then added aluminum chloride with stirring for 4 hours. An appropriate workup yields the alkyl sulfone. (Saikia, P., et al., Chem. Lett., 2001. 512-513.) Reduction of the isoquinoline ring as in Scheme 1 gives a tetrahydroisoquinoline of formula I.

The aryl sulfonyl chloride can also be converted into a diaryl sulfone upon treatment with an appropriate benzene derivative and aluminum chloride according to reported methods (Szmant, H. H. and G. Suld, J. Am. Chem. Soc., 1956. 78: p. 3400-3403. Weijlard, J.; E. F. Swanezy, J. Am. Chem. Soc., 1949. 71: p. 4134-4135) Reduction of the isoquinoline to a tetrahydroisoquinoline of formula I is accomplished in the usual manner as described herein.

SCHEME 8

8A:

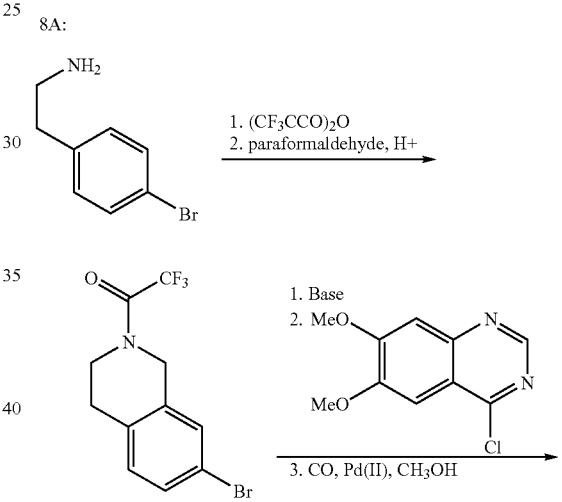

SCHEME 7

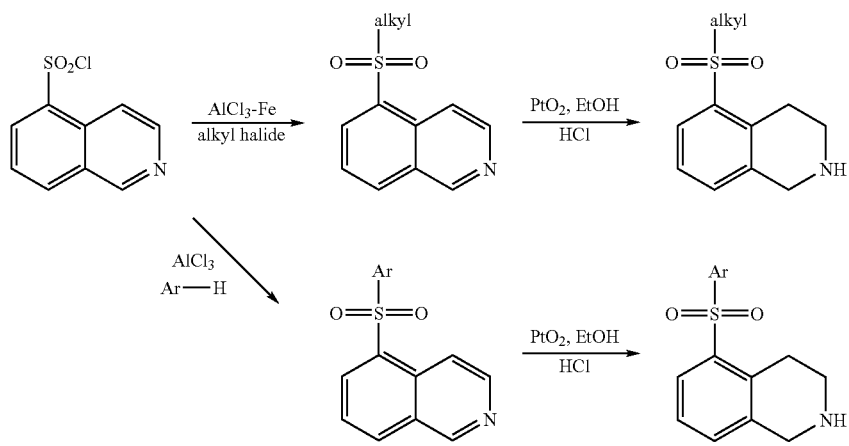

-continued

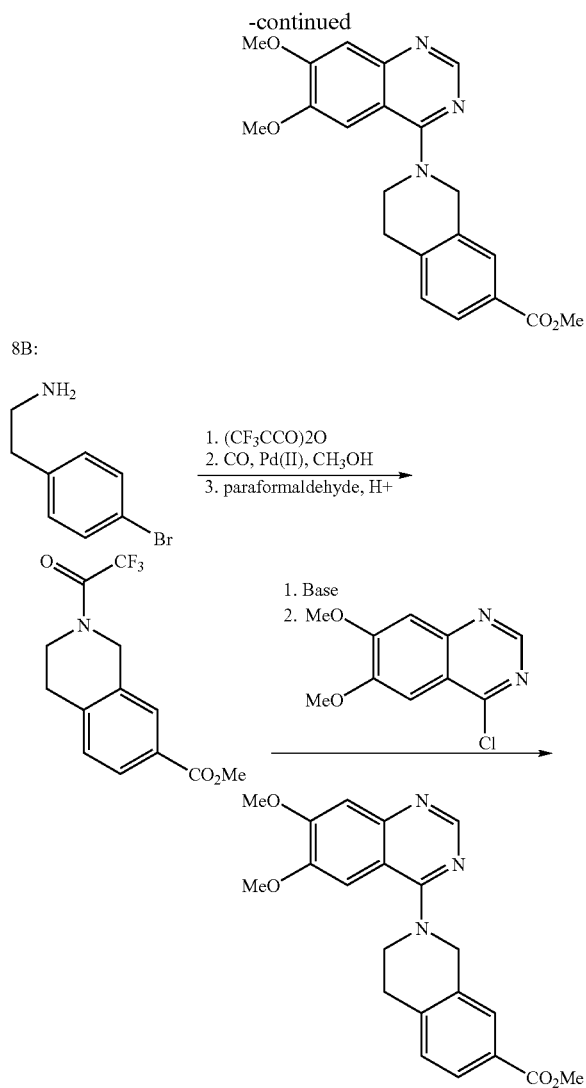

8B:

SCHEME 8B

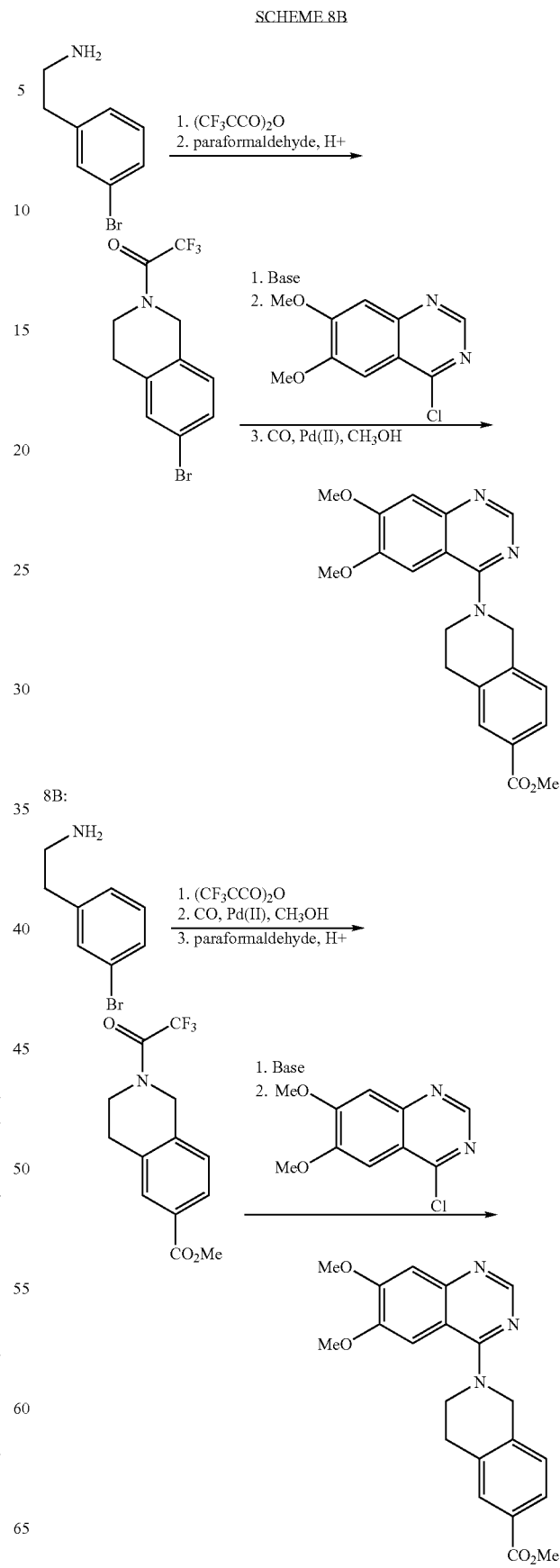

Scheme 8 depicts a method for the preparation of 2-(6, 7-Dimethoxy-quinazolin-4-yl)-1,2,3,4-tetrahydro-isoquinoline-7-carboxylic acid methyl ester. By this method, a substituted phenethylamine is trifluoroacetylated and treated with paraformaldehyde under acidic conditions as described in the literature. (Stoker, G. E., Tetrahedron Lett., 1996. 37(31): p. 5453-5456.)

Cleavage of the trifluoroacetyl group with base under standard conditions (Kocienski, P. J., Protecting Groups. 1994, New York: Georg Thieme Verlag Stuttgart; Greene, T. W. and P. G. M. Wuts, Protective Groups in Organic Synthesis. 1999, New York: John Wiley & Sons) and addition to substituted 4-chloroquinazoline is followed by palladium II mediated coupling with carbon monoxide in methanol to provide the desired ester. In an alternative procedure, shown in Scheme 8B, the order of events is changed: initial trifluoroacetylation is followed by coupling with carbon monoxide. (Fernandez-Gacio, A., C. Vitale and A. Mourino, J. Org. Chem., 2000.65: p. 6978-6983.)

Cyclization is then induced by acid-catalyzed condensation with paraformaldehyde. Cleavage of the trifluoroacetyl group as above and coupling with the substituted 4-chloroquinazoline gives the desired ester.

Scheme 8B depicts a method for the preparation of 2-(6,7-dimethoxy-quinazolin-4-yl)-1,2,3,4-tetrahydro-isoquinoline-6-carboxylic acid methyl ester. This method is performed similarly to the sequence shown in Scheme 8 except that 2-(3-bromo-phenyl)-ethylamine is used as the starting material.

SCHEME 9

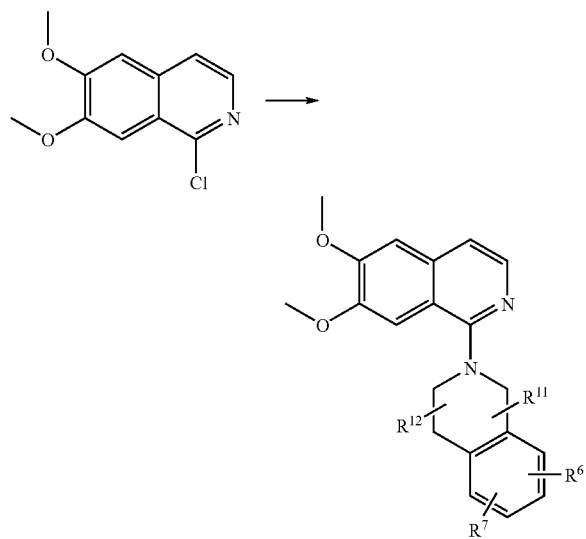

Scheme 9 above depicts a method for the synthesis of dihydro-1'H-[1,2']biisoquinolinyl compounds. According to this method, in what is known as palladium-catalyzed amination reaction, 1-chloro-6,7-dimethoxy-isoquinoline is heated with the appropriate substituted tetrahydroisoquinoline in the presence of palladium acetate and an appropriate ligand such as BINAP. Suitable solvents include but are not limited to benzene, toluene, and xylene, and effective temperatures range from room temperature to 160° C., with 80° C. to 120° C. being particularly effective. This amination reaction can be accomplished through a variety of other coupling methods. (Hartwig, J. F., *Palladium-Catalyzed Amination of aryl halides: mechanism and rational catalyst design*. Synlett, 1996: p. 329-340).

Substituted tetrahydroisoquinolines can be prepared several well known methods. Three of these methods are shown in Schemes 10, 11, and 12. Scheme 10 Illustrates a method for their formation via catalytic hydrogenation of the corresponding substituted isoquinoline. The hydrogenation reaction is commonly known to those skilled in the art.

SCHEME 10

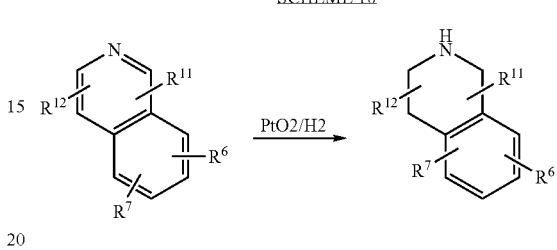

Scheme 11 illustrates another literature route to substituted tetrahydroisoquinolines.[1] According to this method a benzylic aldehyde or ketone is combined with an alpha-amino acid ester in a well-known reductive amination reaction. The resultant benzylamine is induced to cyclize via treatment with a strong acid such as trifluoromethanesulfonic or sulfuric acid to give a substituted tetrahydroisoquinoline product possessing a 4-oxo-substituent. This oxo-substituent can be retained or may be reduced to the corresponding hydroxyl compound via hydrogenation catalyzed by palladium on carbon. The hydroxyl group may likewise be retained or removed via reductive cleavage utilizing more forceful conditions. Alkyl groups may be introduced into the 4-position by subjecting the 4-oxo-product to the well-known Grignard and/or Wittig reactions followed by optional reduction. The cyclization reaction shown in Scheme 11 is substrate-dependent, and the results can vary depending on the nature of $R^5$ and $R^6$.

SCHEME 11

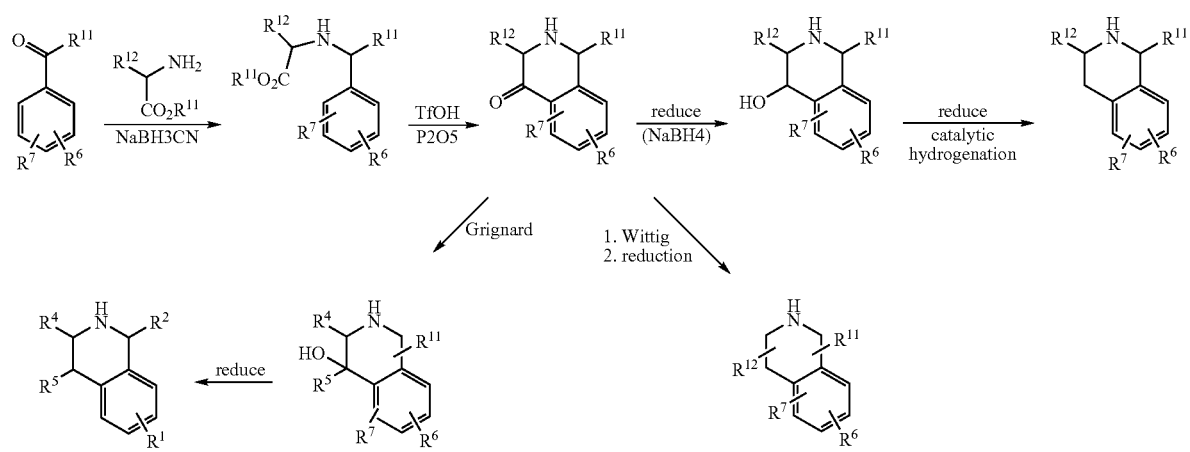

An alternative method for preparing the substituted isoquinoline utilizes the well-known Pictet-Spengler reaction, shown in Scheme 12. Modified Pictet-Spengler reactions have been reported and can improve the product yields in difficult cases.

SCHEME 12

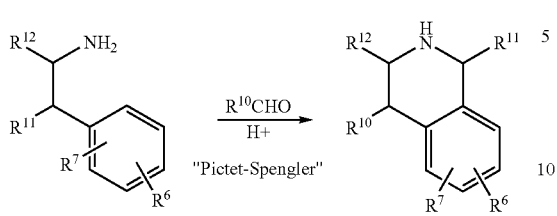

"Pictet-Spengler"

The compound of formula I may have optical centers (e.g. at the ring carbon atoms attached to $R^{10}$ and $R^{12}$) and thus may occur in different enantiomeric configurations. The invention includes all enantiomers, diastereomers, and other stereoisomers and optical isomers of compounds of formula I as well as racemic mixtures thereof.

SCHEME 13

Scheme 13 depicts a coupling reaction between 4-chloro-6,7,8-trimethoxyquinazoline [PC Int. Appl. 2003008388, 30 Jan. 2003] and an $R^3$ derivative of tetrahydroisoquinoline to generate the trimethoxy substituted compound of formula I. This reaction is typically carried out in an inert solvent such as, for example, toluene, optionally in the presence of a carbonate base, at a temperature range of from about 0° C. to about 200° C. Other suitable solvents include benzene, chloroform, dioxane, ethyl acetate, 2-propanol and xylene. Alternatively, solvent mixtures such as toluene/isopropanol can be used. Preferably the reactants are heated under reflux in a solvent mixture of toluene and isopropanol for a period of from about 2 hours to about 24 hours.

SCHEME 14

Scheme 14 depicts the formation of 6-chloro-4-methoxy-[1,3]dioxolo[4,5-h]quinazoline (8) from methyl 4-bromo-7-methoxybenzo[d][1,3]dioxole-5-carboxylate (4). The intermediate, 4-bromo-7-methoxybenzo[d][1,3]dioxole-5-carboxylate, may be made by methods described in the prior art. See Chang, J., et al., *Efficient Synthesis of g-DDB. Bioorg. Med. Chem. lett.*, 2004. 14: p. 2131-2136. The aryl bromide 4 is converted into the carboxylic acid 5 by treatment with a hydroxide base, such as sodium hydroxide or potassium hydroxide, in aqueous solution. This reaction is conducted at temperatures ranging from 0° C. to 100° C. Alternatively, the reaction may be mediated by carbonate bases such as potassium carbonate or sodium carbonate in water at comparable temperatures. The carboxylic acid is then converted into the aniline 6 via a nucleophilic aromatic substitution reaction with ammonia at elevated temperatures. According to this method, the aryl bromide could be treated with ammonia in aqueous or alcoholic solution at temperatures ranging between 100 and 300° C. Alternatively, a copper catalyst such as copper oxide may be used to facilitate the reaction. The resultant aniline is then converted into the quinazolinone 7 on treatment in formamide at a temperature of 100-160° C. Generally, this reaction is conducted with excess formamide that also functions as the solvent. This reaction is known as the Niementowski reaction. Conversion into the requisite 4-chloroquinazoline 8 is finally brought about upon heating to 100-200° C. as a solution in phosphorous oxychloride.

SCHEME 15

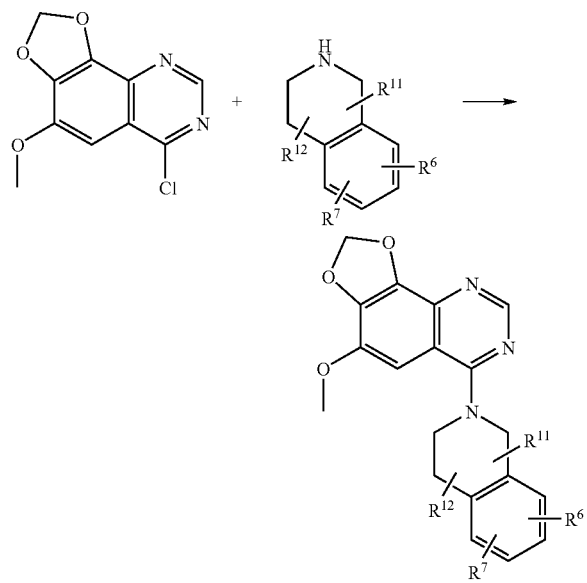

Scheme 15 depicts a coupling reaction between 6-chloro-4-methoxy-[1,3]dioxolo[4,5-h]quinazoline and a derivative of tetrahydroisoquinoline to generate the 4-methoxy-[1,3]dioxolo[4,5-h]quinazoline compound of formula I. This reaction is typically carried out in an inert solvent such as, for example, toluene, optionally in the presence of a carbonate base, at a temperature range of from about 0° C. to about 200° C. Other suitable solvents include benzene, chloroform, dioxane, ethyl acetate, 2-propanol and xylene. Alternatively, solvent mixtures such as toluene/isopropanol can be used. Preferably the reactants are heated under reflux in a solvent mixture of toluene and isopropanol for a period of from about 2 hours to about 24 hours.

The compounds of formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt was obtained.

The acids which are used to prepare the pharmaceutically acceptable acid addition salts of the base compounds of this invention are those which form non-toxic acid addition salts, e.g. salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate, i.e., 1,1'-methylene-bis-(2-hydroxy-3-naphthoate), salts.

The compound of the invention may be administered either alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed thereby can then be readily administered in a variety of dosage forms such as tablets, powders, lozenges, liquid preparations, syrups, injectable solutions and the like. These pharmaceutical compositions can optionally contain additional ingredients such as flavorings, binders, excipients and the like. Thus, the compound of the invention may be formulated for oral, buccal, intranasal, parenteral (e.g. intravenous, intramuscular or subcutaneous), transdermal (e.g. patch) or rectal administration, or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration, the composition may take the form of tablets or lozenges formulated in conventional manner.

The compounds of the invention may be formulated for parenteral administration by injection, including using conventional catheterization techniques or infusion. Formulations for injection may be presented in unit dosage form, e.g. in ampules or in multi-dose containers, with an added preservative. They may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

When a product solution is required, it can be made by dissolving the isolated inclusion complex in water (or other aqueous medium) in an amount sufficient to generate a solution of the required strength for oral or parenteral administration to patients. The compounds may be formulated for fast dispersing dosage forms (fddf), which are designed to release the active ingredient in the oral cavity. These have often been formulated using rapidly soluble gelatin-based matrices. These dosage forms are well known and can be used to deliver a wide range of drugs. Most fast dispersing dosage forms utilize gelatin as a carrier or structure-forming agent. Typically, gelatin is used to give sufficient strength to the dosage form to prevent breakage during removal from packaging, but once placed in the mouth, the gelatin allows immediate dissolution of the dosage form. Alternatively, various starches are used to the same effect.

The compounds of the invention may also be formulated in rectal compositions such as suppositories or retention enemas, e.g. containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made e.g. from gelatin) for use in an inhaler or insufflator may be formulated containing a powder mix of a compound of the invention and a suitable powder base such as lactose or starch.

Aerosol formulations for treatment of the conditions referred to above (e.g. migraine) in the average adult human are preferably arranged so that each metered dose or "puff" of aerosol contains about 20 mg to about 1000 mg of the compound of the invention. The overall daily dose with an aerosol will be within the range of about 100 mg to about 10 mg. Administration may be several times daily, e.g. 2, 3, 4 or 8 times, giving for example, 1, 2 or 3 doses each time.

A proposed daily dose of the compound of the invention for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

Assay methods are available to screen a substance for inhibition of cyclic nucleotide hydrolysis by the PDE 10 and the PDEs from other gene families. The cyclic nucleotide substrate concentration used in the assay is ⅓ of the $K_m$ concentration, allowing for comparisons of $IC_{50}$ values across the different enzymes. PDE activity is measured using a Scintillation Proximity Assay (SPA)-based method as previously described (Fawcett et al., 2000). The effect of PDE inhibitors is determined by assaying a fixed amount of enzyme (PDEs 1-11) in the presence of varying substance concentrations and low substrate, such that the $IC_{50}$ approximates the $K_i$ (cGMP or cAMP in a 3:1 ratio unlabelled to [$^3$H]-labeled at a concentration of ⅓ Km).). The final assay volume is made up to 100 µl with assay buffer [20 mM Tris-HCl pH 7.4, 5 mM $MgCl_2$, 1 mg/ml bovine serum albumin]. Reactions are initiated with enzyme, incubated for 30-60 min at 30° C. to give <30% substrate turnover and terminated with 50 µl yttrium silicate SPA beads (Amersham) (containing 3 mM of the respective unlabelled cyclic nucleotide for PDEs 9 and 11). Plates are re-sealed and shaken for 20 min, after which the beads were allowed to settle for 30 minutes in the dark and then counted on a TopCount plate reader (Packard, Meriden, Conn.) Radioactivity units can be converted to percent activity of an uninhibited control (100%), plotted against inhibitor concentration and inhibitor $IC_{50}$ values can be obtained using the "Fit Curve" Microsoft Excel extension.

The following examples are illustrative of the invention, but are not intended to limit the scope of the claimed invention.

Examples are preceded by preparative examples that are used to prepare certain starting materials.

EXAMPLES

Preparation 1

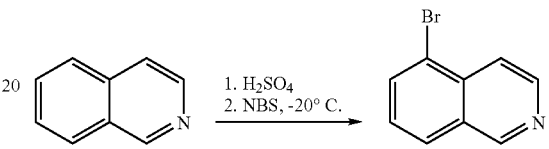

Bromination of Isoquinoline (Brown, William Dalby; Gouliaev, Alex-Haahr. Synthesis (2002), (1), p. 83-86.

Preparation 2

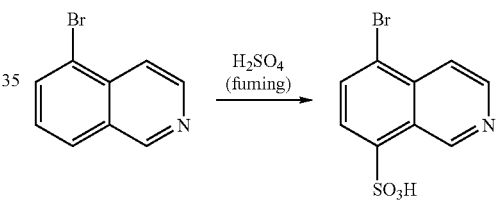

5-Bromoisoquinoline-8-sulfonic acid

To fuming sulfuric acid at 0° C. was added 5-bromoisoquinoline (20.0 g, 96 mmol), The resultant mixture was warmed to 200° C. for 4 h and was then cooled to rt and poured into 500 mL of ice water. The product was removed via filtration, washed with water and acetone, and dried to give 25 g (90%) of a white solid.

Preparation 3

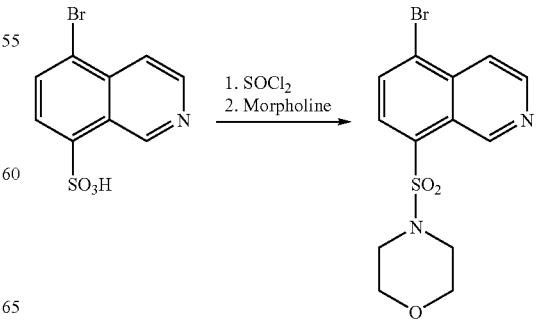

5-Bromo-8-(morphine-4-sulfonyl)-isoquinoline

To 5-bromoisoquinoline-8-sulfonic acid (68.0 g, 236 mmol) in dimethylformamide (310 mL) was added SOCl₂ (270 mL). the mixture was heated to reflux for 6 h, and cooled to rt. Excess SOCl₂ was removed via evaporation. Methylene chloride (400 mL) was added and the mixture was cooled to 0° C. Morpholine (62 mL) was added slowly as a solution in 50 mL of CH₂Cl₂, and the resultant mixture was warmed to room temperature and stirred for 1 hour The mixture was diluted with aqueous ammonia and extracted with CH₂Cl₂. The extracts were dried with Na₂SO₄ and concentrated. Flash chromatography eluting with CH₂Cl₂/EtOAc/hexanes afforded 27.3 g (35%) of the title compound. Treatment of the aqueous phase with acid and filtration of the resultant precipitate provided 29.9 g (43%) of recovered staring material.

Preparation 4

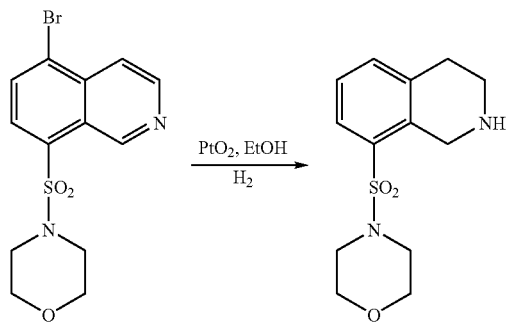

8-(Morpholine-4-sulfonyl)-1,2,3,4-tetrahydro-isoquinoline

To 16.0 g (48 mmol) of 5-Bromo-8-(morpholine-4-sulfonyl)-isoquinoline in warm EtOH (120 mL) in a Par bottle under an atmosphere of nitrogen was added PtO₂ (2.0 g). The mixture was hydrogenated at 50 psi. for 4 h at 60° C. The hydrogen atmosphere was replace with nitrogen and an additional 2.0 g of catalyst was added. The hydrogenation was repeated as above. After 4 h the catalyst was carefully removed via filtration and the resultant solution was concentrated to yield a solid. The solid was treated with aqueous ammonia and extracted with CH₂Cl₂. The extracts were dried and concentrated. Flash chromatography (0.1:3:97 NH₄OH/MeOH/CH₂Cl₂) gave 6.2 g (52%) of the title compound.

Example 1

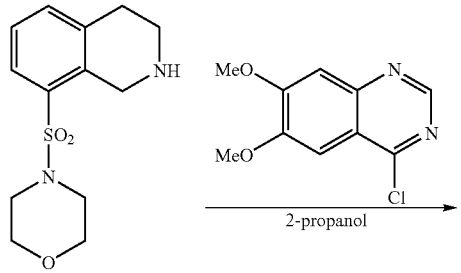

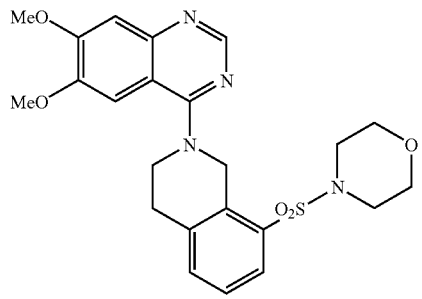

6,7-dimethoxy-4-[8-(morpholine-4-sulfonyl)-3,4-dihydro-1H-isoquinolin-2-yl]-quinazoline 8-(morpholine-4-sulfonyl)-1,2,3,4-tetrahydroisoquinoline (15.7 g, 55.6 mmol) and 4-chloro-6,7-dimethoxy-quinazoline (12.5 g, 55.6 mmol) were refluxed overnight in 2-propanol (400 mL). The solvent was removed under vacuum and the resultant solid was partitioned between aqueous ammonia and CH₂Cl₂. The mixture was extracted three times with CH₂Cl₂ and the combined extracts were dried and concentrated. Flash chromatography (0.1:3:97 NH₄OH/MeOH/CH₂Cl₂) followed by recrystallization of the product fractions from EtOH provided, in two crops, 22.2 g (85%) of the title compound.

Example 2

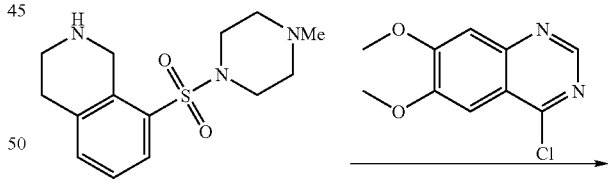

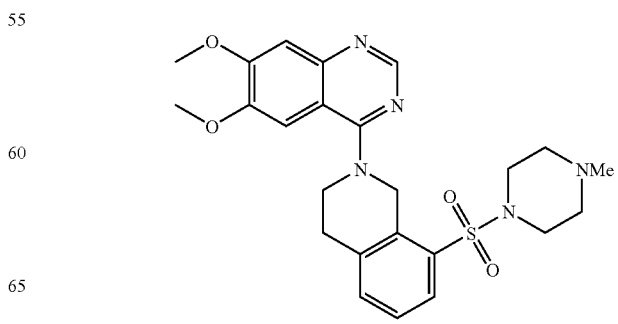

6,7-dimethoxy-4-[8-(4-methyl-piperazine-1-sulfonyl)-3,4-dihydro-1H-isoquinolin-2-yl]-quinazoline This compound was prepared according to the procedure of Example 1.

(4-bromo-benzylamino)-acetic acid

To (4-bromo-benzylamino)-acetic acid methyl ester (100 mg, 0.342 mmol) in water (3 mL) was added lithium hydroxide (57 mg, 0.684 mmol). After 4 hours the solution was partially quenched with 1 M HCl (1.5 mL) to give a solution pH of ca 8.5. The pH of the solution was carefully adjusted to pH 5 by the addition of 3-4 drops of 1 M HCl. Stirring overnight yielded a white precipitate. This was isolated via filtration, rinsing with a small amount of cold water, to give the desired zwitterion.

Example 3

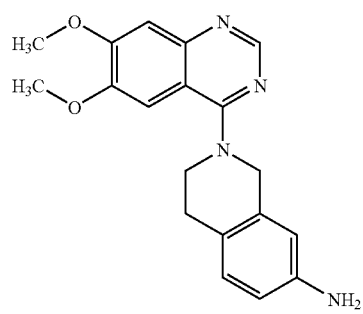

2-(6,7-Dimethoxy-quinazolin-4-yl)-1,2,3,4-tetrahydro-isoquinolin-7-ylamine

Mass spectrum m/e calcd. for M+H=337.5. Found 337.2.

Example 4

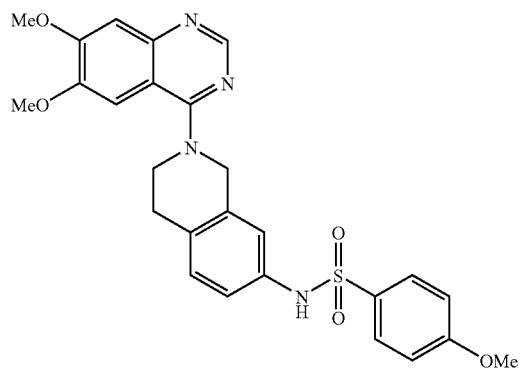

N-[2-(6,7-Dimethoxyquinazolin-4-yl)-1,2,3,4-tetrahydro-isoquinolin-7-yl]-4-methoxy-benzenesulfonamide To 2-(6,7-dimethoxy-quinazolin-4-yl)-1,2,3,4-tetrahydro-isoquinoline-7-ylamine (51 mg, 150 mmol) in chloroform (1 mL) was added triethylamine (76 mg, 750 mmol) followed by 4-methoxy-benzenesulfonyl chloride (40 mg, 165 mmol). When complete by TLC analysis, the mixture was quenched with water and extracted with chloroform. The extracts were dried, concentrated, and chromatographed via silica gel chromatography eluting with ethanol/ethyl acetate. The product was treated with HCl/ether to yield the hydrochloride salt as a white solid. Mass spectrum m/e calcd. for M+H=507.8. Found 507.2.

Example 5

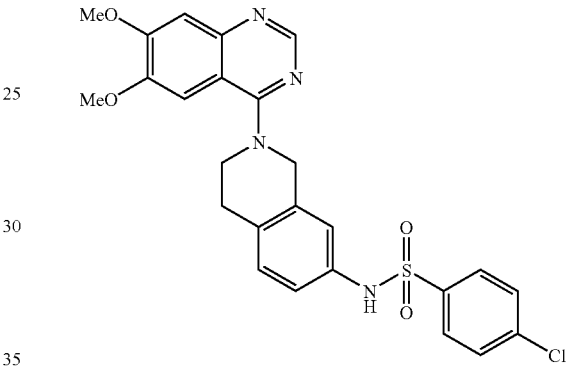

4-Chloro-N-[2-(6,7-dimethoxy-quinazolin-4-yl)-1,2,3,4-tetrahydro-isoquinolin-7-yl]-benzenesulfonamide Mass spectrum m/e calcd. for M+H=512.1. Found 512.3. This compounds was prepared similarly to Example 1.

Example 6

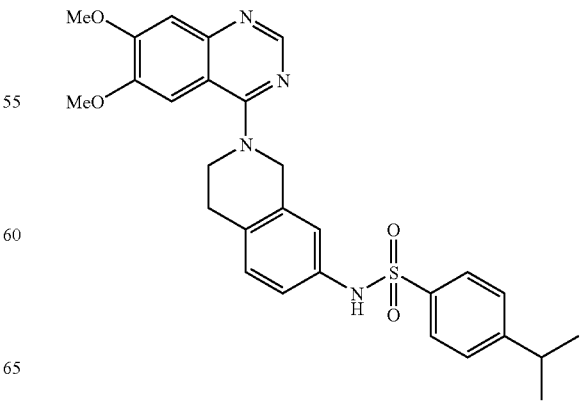

N-[2-(6,7-dimethoxy-quinazolin-4-yl)-1,2,3,4-tetrahydro-isoquinolin-7-yl]-4-isopropyl-benzenesulfonamide Mass spectrum m/e calcd. for M+H=519.7. Found 519.2.

Example 7

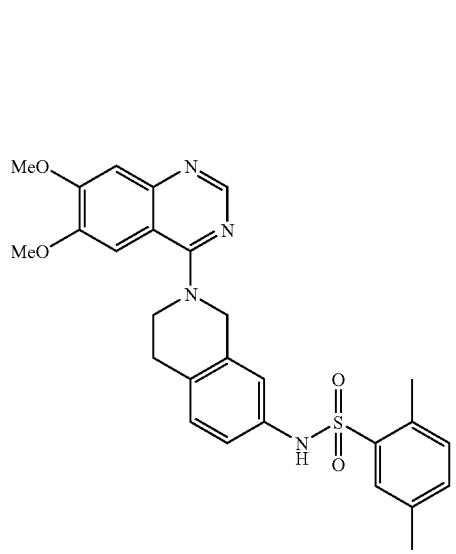

N-[2-(6,7-dimethoxy-quinazolin-4-yl)-1,2,3,4-tetrahydro-isoquinolin-7-yl]-2,5-dimethyl-benzenesulfonamide Mass spectrum m/e calcd. for M+H=505.7. Found 505.1.

Example 8

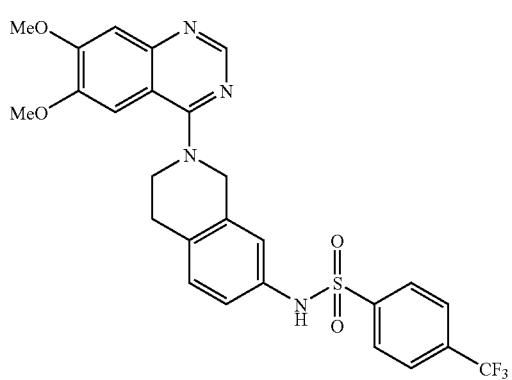

N-[2-(6,7-dimethoxy-quinazolin-4-yl)-1,2,3,4-tetrahydro-isoquinolin-7-yl]-4-trifluoromethyl-benzenesulfonamide Mass spectrum m/e calcd. for M+H=545.7. Found 545.6.

Example 9

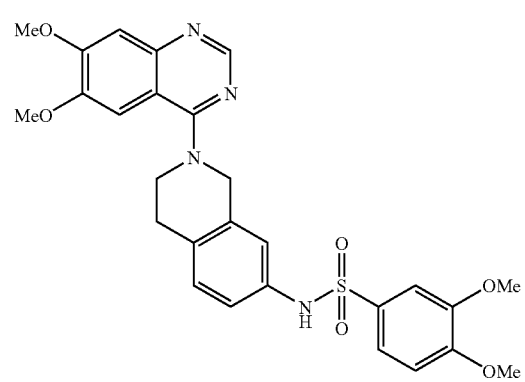

N-[2-(6,7-dimethoxy-quinazolin-4-yl)-1,2,3,4-tetrahydro-isoquinolin-7-yl]-3,4-dimethoxy-benzenesulfonamide Mass spectrum m/e calcd. for M+H=537.7. Found 537.8.

Example 10

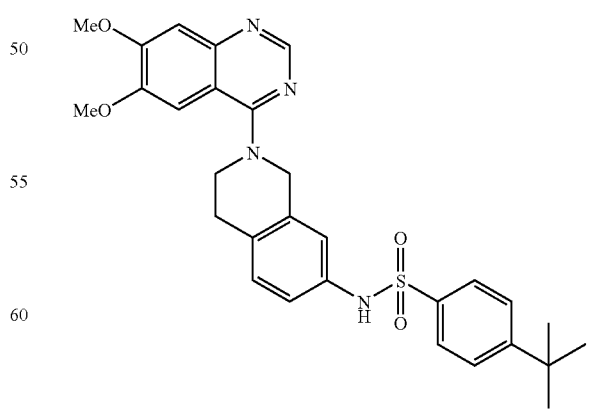

4-tert-Butyl-N-[2-(6,7-dimethoxy-quinazolin-4-yl)-1,2,3,4-tetrahydro-isoquinolin-7-yl]-benzenesulfonamide Mass spectrum m/e calcd. for M+H=533.8. Found 533.7.

Example 11

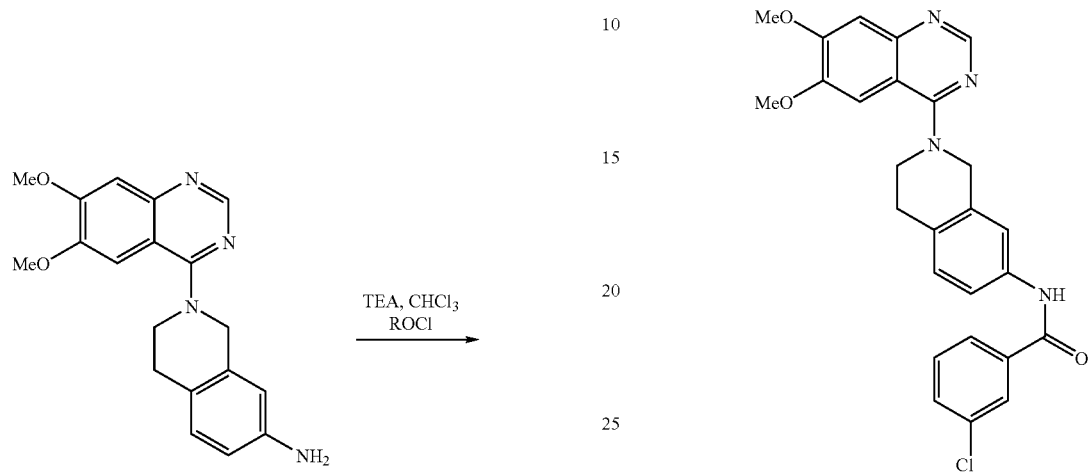

N-[2-(6,7-dimethoxyquinazolin-4-yl)-1,2,3,4-tetrahydroisoquinolin-7-yl]-4-ethoxy benzamide To the aniline (100 mg, 0.30 mmol) in CHCl3 (1.0 mL) was added triethylamine (91 mg, 0.90 mmol) followed by the acid chloride (0.33 mmol). The reaction was stirred at room temperature until complete by TLC analysis at which point the mixture was quenched with water and extracted with chloroform. The extracts are combined, dried, concentrated and chromatographed (EtOH/EtOAc) gave the title compound as an orange oil. Treatment with HCl/ether provided the hydrochloride salt as a white solid. Mass spectrum m/e calcd. for M+H=485.4. Found 485.3.

Example 12

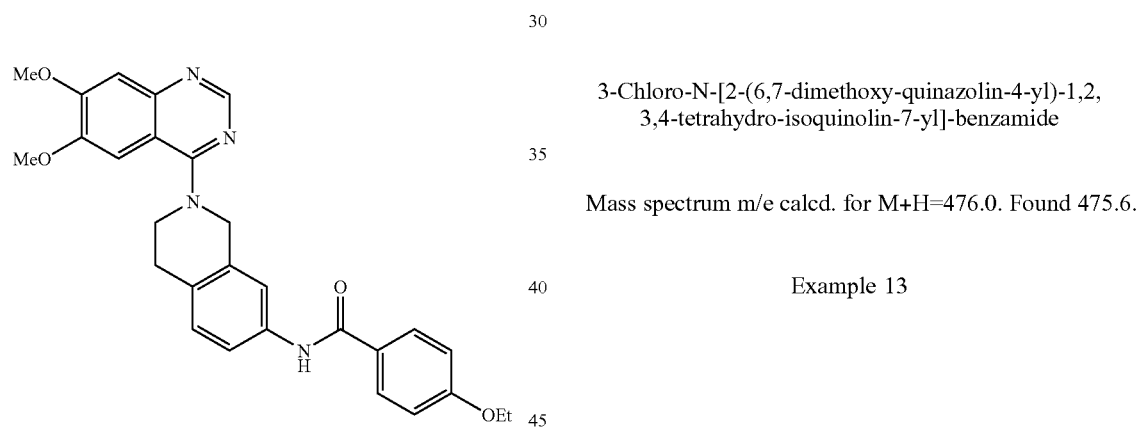

3-Chloro-N-[2-(6,7-dimethoxy-quinazolin-4-yl)-1,2,3,4-tetrahydro-isoquinolin-7-yl]-benzamide Mass spectrum m/e calcd. for M+H=476.0. Found 475.6.

Example 13

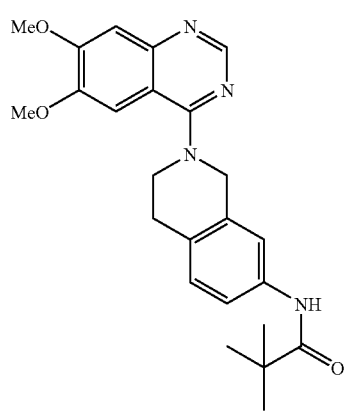

39

N-[2-(6,7-Dimethoxy-quinazolin-4-yl)-1,2,3,4-tetrahydro-isoquinolin-7-yl]-2,2-dimethyl-propionamide Mass spectrum m/e calcd. for M+H=421.6. Found 421.2.

Example 14

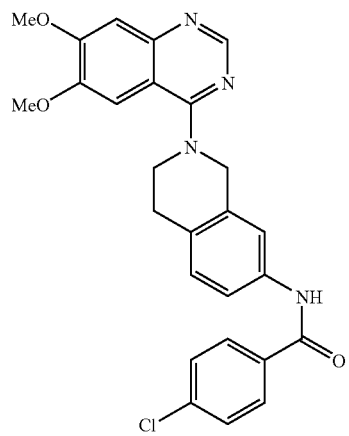

4-Chloro-N-[2-(6,7-dimethoxy-quinazolin-4-yl)-1,2,3,4-tetrahydro-isoquinolin-7-yl]-benzamide Mass spectrum m/e calcd. for M+H=476.0. Found 475.1.

Example 15

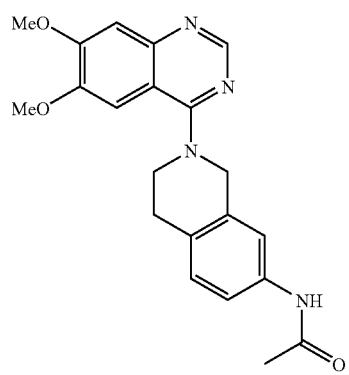

40

N-[2-(6,7-Dimethoxy-quinazoline-4-yl)-1,2,3,4-tetrahydro-isoquinolin-7-yl]-acetamide Mass spectrum m/e calcd. for M+H=379.5. Found 379.2.

Example 16

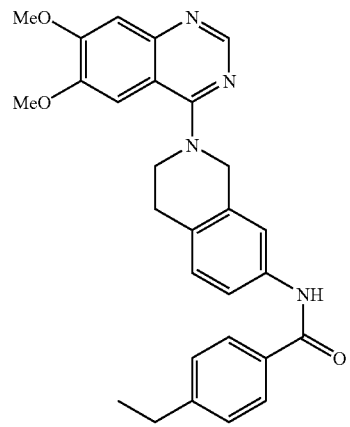

N-[2-(6,7-Dimethoxy-quinazolin-4-yl)-1,2,3,4-tetrahydro-isoquinolin-7-yl]-4-ethyl-benzamide Mass spectrum m/e calcd. for M+H=469.7. Found 469.3.

Example 17

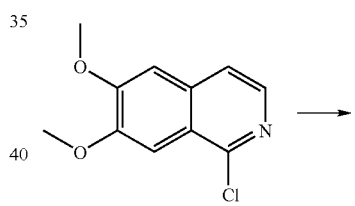

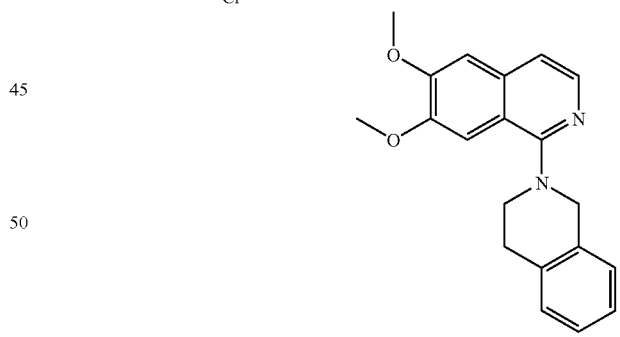

6,7-Dimethoxy-3',4'-dihydro-1'H-[1,2']biisoquinolinyl.

Palladium acetate (25 mg 0.112 mmol) and 2,2'-bis(diphenylphosphino)-1,1'-binaphtyl (209 mg, 0.335 mmol) were heated to 80° C. in toluene (25 mL) for 20 min. To the mixture was added 500 mg (2.24 mmol) of 1-chloro-6,7-dimethoxy-isoquinoline, 298 mg (2.24 mmol) of tetrahydroisoquinoline, and 4.47 mL (4.47 mmol) of a 1.0 M solution of potassium tert-butoxide in THF. After stirring at reflux for 4 h, the mixture was diluted with EtOAc, washed with water, dried over MgSO4 and concentrated. Silica gel chromatography (4:1 hexanes/EtOAc) provided 625 mg (87%) of the title compound as a yellow oil. The hydrochloride salt (387 mg) was obtained after treatment with concd. HCl in isopropanol and recrystallization from EtOH/MeOH.

What is claimed is:

1. A compound having the formula

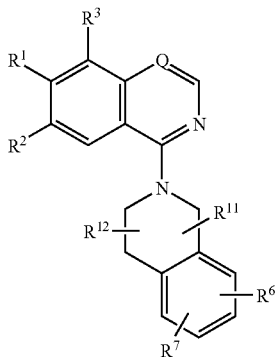

I or a pharmaceutically acceptable salt, solvate or thereof, wherein Q is N or CH;

wherein $R^1$, $R^2$ and $R^3$ are each independently hydrogen, halogen, $(C_1-C_9)$alkyl, $(C_2-C_9)$ alkenyl, $(C_2-C_9)$ alkynyl, $(C_3-C_8)$cycoloalkyl, —O—$(C_1-C_9)$ alkyl, —O—$(C_2-C_9)$ alkenyl, $(C_1-C_6)$alkyl O—$(C_1-6)$alkyl, —C≡N, —$NO_2$, —$COOR^4$, —$CONR^4R^5$, —$NR^4R^5$, $COR^5$, or —COOH wherein said alkyl, alkenyl and alkynyl are optionally substituted with 1 to 3 halogens; wherein $R^4$ and $R^5$ are independently H, $C_1$-$C_6$ alkyl, or $(C_2$-$C_6)$alkenyl) wherein said alkyl and alkenyl are optionally substituted with from 1 to 3 halogen atoms; and, when $R^1$, $R^2$ and $R^3$ are independently —O-alkyl, —O-alkenyl, or alkyl, alkenyl or alkynyl, $R^2$ and $R^1$ or $R^1$ and $R^3$ may optionally be connected to form a methylenedioxy group;

$R^6$ is hydrogen;

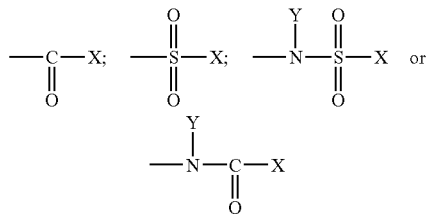

$R^7$ is

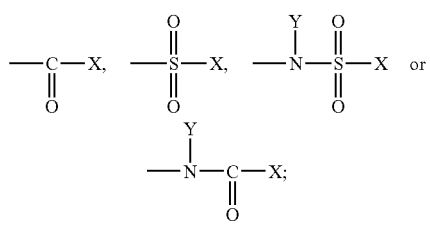

wherein X is a $C_1$-$C_6$ alkyl group unsubstituted or substituted with one or more halogens, —O—$C_1$-$C_6$ alkyl unsubstituted or substituted with one or more halogens, a $(C_6$-$C_{14})$ aryl group unsubstituted or substituted with one or two substituents, a —$NR^8R^9$ group or

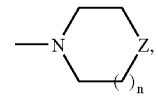

wherein said $(C_6$-$C_{14})$ aryl group substituents are independently selected from $C_1$-$C_6$ alkyl, —O—$C_1$-$C_6$ alkyl, halogen, —C≡N, —$NO_2$, —$COOR^4$, —$CONR^4R^5$, —$NR^4R^5$, —$COR^4$, and —COOH, and $(C_1$-$C_6)$alkyl substituted with 1 to 3 halogens;

Y is hydrogen or $(C_1$-$C_6)$alkyl;

n is 0 or 1;

$R^8$ and $R^9$ are each independently $(C_1$-$C_6)$alkyl or hydrogen;

Z is oxygen or $NR^{10}$, wherein $R^{10}$ is hydrogen or $(C_1$-$C_6)$alkyl;

wherein $R^{11}$ and $R^{12}$ are independently H, halogen, C≡N, —COOH, —$COOR^4$, —$CONR^4R^5$, $COR^4$, —$NR^4R^5$, —OH, $(C_6$-$C_{14})$ aryl, 5 to 12 membered heteroaryl, $(C_1$-$C_6)$ alkyl, $(C_2$-$C_6)$ alkenyl, $(C_2$-$C_6)$ alkynyl or $(C_3$-$C_8)$ cycloalkyl wherein said alkyl, alkenyl, and alkynyl are optionally independently substituted with from 1 to 3 halogens.

2. The compound of claim 1 wherein Q is N and $R^1$ and $R^2$ are each —$OCH_3$.

3. The compound of claim 1 wherein Q is N and $R^1$ and $R^2$ are each —$OCH_3$ and one or both of $R^6$ and $R^7$ are

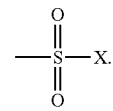

4. The compound of claim 3 wherein X is 4-methyl piperazine.

5. The compound of claim 1 wherein Q is N, $R^1$ and $R^2$ are each —$OCH_3$ and one or both of $R^6$ and $R^7$ are

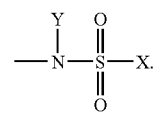

6. The compound of claim 5 wherein Y is hydrogen and X is mono- or disubstituted aryl.

7. The compound of claim 6 wherein Y is hydrogen and X is phenyl or naphthyl, optionally substituted with $C_1$-$C_6$ alkyl, $C_1$-$C_6$ alkoxy, —C≡N, —$NO_2$, —$COOR^4$, $CONR^4R^5$, —$NR^4R^5$, —$COR^4$, and —COOH.

8. The compound of claim 1 wherein Q is N, $R^1$ and $R^2$ are each —$OCH_3$, and one or both of $R^6$ and $R^7$ are

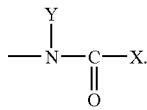

9. The compound of claim 1 wherein Q is OH, $R^1$ and $R^2$ are each —$OCH_3$ and $R_6$, $R_7$, $R_{11}$ and $R_{12}$ are hydrogen.

10. The compound of claim 1 wherein Q is N and $R^{11}$ and $R^{12}$ are independently selected from hydrogen, ($C_1$-$C_6$) alkyl, ($C_2$-$C_6$) alkenyl, ($C_2$-$C_6$) alkynyl and ($C_3$-$C_8$)cycloalkyl.

11. A compound according to claim 1 selected from the group consisting of:
   4-chloro-N-[2-(6,7-dimethoxy-quinazolin-4-yl)-1,2,3,4-tetrahydro-isoquinolin-7-yl]-benzenesulfonamide;
   N-[2-(6,7-dimethoxy-quinazolin-4-yl)-1,2,3,4-tetrahydro-isoquinolin-7-yl]-4-isopropyl-benzenesulfonamide;
   N-[2-(6,7-dimethoxy-quinazolin-4-yl)-1,2,3,4-tetrahydro-isoquinolin-7-yl]-2,5-dimethyl-benzenesulfonamide;
   N-[2-(6,7-dimethoxy-quinazolin-4-yl)-1,2,3,4-tetrahydro-isoquinolin-7-yl]-2,2-dimethyl-propionamide;
   N-[2-(6,7-dimethoxy-quinazoline-4-yl)-1,2,3,4-tetrahydro-isoquinolin-7-yl]-acetamide;
   N-[2-(6,7-dimethoxy-quinazolin-4-yl)-1,2,3,4-tetrahydro-isoquinolin-7-yl]-4-ethyl-benzamide;
   4-chloro-N-[2-(6,7-dimethoxy-quinazolin-4-yl)-1,2,3,4-tetrahydro-isoquinolin-7-yl]-benzamide;
   3-chloro-N-[2-(6,7-dimethoxy-quinazolin-4-yl)-1,2,3,4-tetrahydro-isoquinolin-7-yl]-benzamide;
   4-tert-butyl-N-[2-(6,7-dimethoxy-quinazolin-4-yl)-1,2,3,4-tetrahydro-isoquinolin-7-yl]-benzenesulfonamide;
   N-[2-(6,7-dimethoxyquinazolin-4-yl)-1,2,3,4-tetrahydroisoquinolin-7-yl]-4-ethoxy benzamide;
   N-[2-(6,7-dimethoxy-quinazolin-4-yl)-1,2,3,4-tetrahydro-isoquinolin-7-yl]-4-trifluoromethyl-benzenesulfonamide.
   N-[2-(6,7-dimethoxy-quinazolin-4-yl)-1,2,3,4-tetrahydro-isoquinolin-7-yl]-3,4-dimethoxy-benzenesulfonamide;
   6,7-dimethoxy-4-[8-(morpholine-4-sulfonyl)-3,4-dihydro-1H-isoquinolin-2-yl]-quinazoline; and
   6,7-dimethoxy-4-[8-(4-methyl-piperazine-1-sulfonyl)-3,4-dihydro-1H-isoquinolin-2-yl]-quinazoline.

12. A compound according to claim 1 selected from the group consisting of:
   6,7,8-Trimethoxy-4-[8-(4-methyl-piperazine-1-sulfonyl)-3,4-dihydro-1H-isoquinolin-2-yl]-quinazoline
   4-Methoxy-6-[8-(4-methyl-piperazine-1-sulfonyl)-3,4-dihydro-1H-isoquinolin-2-yl]-1,3-dioxa-7,9-diaza-cyclopenta[a]naphthalene
   2-(4-Methoxy-1,3-dioxa-7,9-diaza-cyclopenta[a]naphthalen-6-yl)-1,2,3,4-tetrahydro-isoquinoline-7-carboxylic acid amide; and
   2-(6,7,8-Trimethoxy-quinazolin-4-yl)-1,2,3,4-tetrahydro-isoquinoline-7-carboxylic acid amide.

13. A process for preparing a compound of formula I

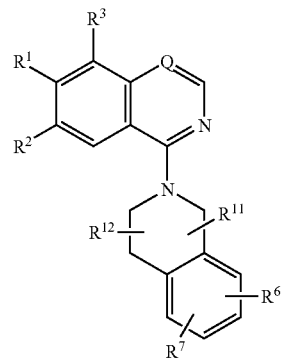

or a pharmaceutically acceptable salt, solvate or thereof,
   wherein Q is N or C;
   wherein $R^1$ and $R^2$ are each independently hydrogen, halogen, ($C_1$-$C_9$)alkyl, ($C_2$-$C_9$) alkenyl, ($C_2$-$C_9$) alkynyl, ($C_3$-$C_8$)cycoloalkyl, —O—($C_1$-$C_9$) alkyl, —O—($C_2$-$C_9$) alkenyl, ($C_1$-$C_6$)alkoxy ($C_1$-$C_6$) alkyl, —C≡N, —$NO_2$, —$COOR^4R^4$, —$CONR^4R^5$, —$NR^4R^5$, —$COR^5$, —COOH wherein said alkyl, alkenyl and alkynyl are optionally substituted with 1 to 3 halogens, wherein $R^4$ and $R^5$ are independently H or $C_1$-$C_6$ alkyl optionally substituted with from 1 to 3 halogen atoms; and,
   when $R^1$ and $R^2$ are independently —O- alkyl or alkyl, $R^1$ and $R^2$ may be connected to form a methylenedioxy group;
   $R^6$ is hydrogen;

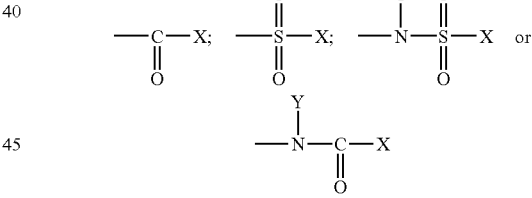

$R^7$ is

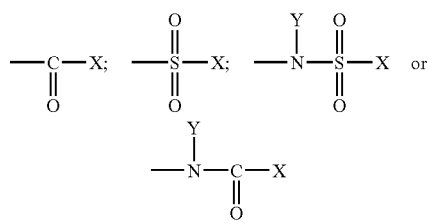

wherein X is a $C_1$-$C_6$ alkyl group unsubstituted or substituted with one or more halogens, a $C_1$-$C_6$ alkoxy group unsubstituted or substituted with one or more halogens, a ($C_6$-$C_{14}$) aryl group unsubstituted or substituted with one or two substituents, a —$NR^8R^9$ group or

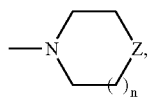

wherein said ($C_6$-$C_{14}$) aryl group substituents are independently selected from $C_1$-$C_{06}$ alkyl, $C_1$-$C_6$ alkoxy, halogen, —C≡N, —$NO_2$, —$COOR^4$, —$CONR^4R^5$, —$NR^4R^5$, —$COR^4$, and —COOH, and ($C_1$-$C_6$)alkyl substituted with 1 to 3 halogens;

Y is hydrogen or ($C_1$-$C_6$)alkyl;

n is 0 or 1;

$R^8$ and $R^9$ are each independently ($C_1$-$C_6$)alkyl or hydrogen;

Z is oxygen or $NR^{10}$, wherein $R^{10}$ is hydrogen or ($C_1$-$C_6$)alkyl;

wherein $R^{11}$ and $R^{12}$ are independently H, halogen, C≡N, —COOH, —$COOR^4$, —$CONR^4R^5$, $COR^4$, —$NR^4$, —$NR^4R^5$, —OH, ($C_6$-$C_{14}$)aryl, 5 to 12 membered heteroaryl, ($C_1$-$C_6$) alkyl or ($C_2$-$C_6$) alkenyl, ($C_2$-$C_6$) alkynyl or ($C_3$-$C_8$) cycloalkyl wherein said alkyl, alkenyl, and alkynyl are optionally independently substituted with from 1 to 3 halogens;

comprising reacting a compound of formula $II_a$

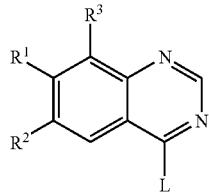

wherein $R^1$ and $R^2$ are each independently hydrogen, halogen, ($C_1$-$C_9$)alkyl, ($C_2$-$C_9$) alkenyl, ($C_2$-$C_9$) alkynyl, ($C_3$-$C_8$)cycoloalkyl, —O—($C_1$-$C_9$) alkyl, —O—($C_2$-$C_9$) alkenyl, ($C_1$-$C_6$) alkoxy ($C_1$-$C_6$)alkyl, —C≡N, —$NO_2$, —$COOR^4$, —$CONR^4R^5$, —$NR^4R^5$, —$COR^5$, —COOH wherein said alkyl, alkenyl and alkynyl are optionally substituted with 1 to 3 halogens, wherein $R^4$ and $R^5$ are independently H or 1-6 alkyl optionally substituted with from 1 to 3 halogen atoms; and, when $R^1$ and $R^2$ are independently —O-alkyl or alkyl, $R^1$ and $R^2$ may be connected to form a methylenedioxy group;

and L is a suitable leaving group; with a compound of formula III

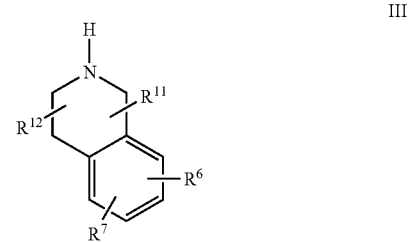

in the presence of a base.

14. The process of claim 13 wherein L is a leaving group comprising a halogen atom selected from chlorine, bromine and iodine.

15. A method of treating a disorder or condition selected from the group consisting of schizophrenia, and psychosis, comprising administering an amount of the compound of claim 1 effective in treating said disorder or condition.

16. The method of claim 15 wherein said disorder or condition is schizophrenia.

* * * * *